US007256179B2

(12) United States Patent
Iyer et al.

(10) Patent No.: US 7,256,179 B2
(45) Date of Patent: Aug. 14, 2007

(54) NUCLEIC ACID-BASED COMPOUNDS AND METHODS OF USE THEREOF

(75) Inventors: Radhakrishnan P. Iyer, Shrewsbury, MA (US); Yi Jin, Pointe Claire (CA); Arlene Roland, Montreal (CA); Wenqiang Zhou, Bedford Hills, NY (US)

(73) Assignee: Migenix, Inc., Vancouver (CA)

( * ) Notice: Subject to any disclaimer, the term of this patent is extended or adjusted under 35 U.S.C. 154(b) by 0 days.

(21) Appl. No.: 11/057,779

(22) Filed: Feb. 14, 2005

(65) Prior Publication Data

US 2005/0143337 A1 Jun. 30, 2005

Related U.S. Application Data

(62) Division of application No. 10/146,175, filed on May 15, 2002, now Pat. No. 6,881,831.

(60) Provisional application No. 60/291,471, filed on May 16, 2001.

(51) Int. Cl.
*A01N 43/04* (2006.01)
*A61K 31/70* (2006.01)
*C07H 19/20* (2006.01)

(52) U.S. Cl. .......................... 514/43; 514/42

(58) Field of Classification Search ................ 514/42, 514/43
See application file for complete search history.

(56) References Cited

U.S. PATENT DOCUMENTS

| 5,212,295 A | 5/1993 | Cook |
| 5,218,103 A | 6/1993 | Caruthers et al. |
| 5,547,941 A | 8/1996 | Battistini et al. |
| 5,614,504 A | 3/1997 | Hadden et al. |
| 5,773,431 A | 6/1998 | Javitt |
| 5,843,912 A | 12/1998 | Hosmane et al. |
| 6,620,796 B1 | 9/2003 | Zhou et al. |

FOREIGN PATENT DOCUMENTS

| DE | 4111730 A1 | 4/1991 |
| FR | 2641537 A1 | 5/2001 |
| WO | WO 90/07520 | 7/1990 |
| WO | WO 90/12578 | 11/1990 |
| WO | WO 92/18520 | 10/1992 |
| WO | WO 94/00472 | 1/1994 |
| WO | WO 94/00473 | 1/1994 |
| WO | WO 94/22864 | 10/1994 |
| WO | WO 95/32984 | 12/1995 |
| WO | WO 96/10030 | 4/1996 |
| WO | WO 96/39154 | 12/1996 |
| WO | WO 96/39413 | 12/1996 |
| WO | WO 96/39502 | 12/1996 |
| WO | WO 97/19092 | 5/1997 |
| WO | WO 98/30575 | 7/1998 |
| WO | WO 99/64378 | 12/1999 |
| WO | WO 01/34622 | 5/2001 |
| WO | WO 01/40515 A1 | 6/2001 |
| WO | WO 2002/043771 A3 | 6/2002 |
| WO | WO 02/081494 A1 | 10/2002 |

OTHER PUBLICATIONS

Matsukura et al. Proc. Natl. Acad. Sci. USA (1987), vol. 84, pp. 7706-7710.*
Zhou, W. et al., "Combinatorial Synthesis using nucleic acid-based NAB™ scaffold: parallel solid-phase synthesis of nucleotide libraries," *Tetrahedron Letters*, 41:441-445 (2000).
Davis, Peter W. et al., Communications to the Editor: "Drug Leads from Combinatorial Phosphodiester Libraries," *Med. Chem.*, 38:4363-4366 (1995).
International Search Report (May 2001).
Moriguchi et al. Chemical Abstracts, vol. 131:228913 (1999).
Ma et al., Chemical Abstracts, vol. 11:133624 (1995).
Cummins et al., Chemical Abstracts, vol. 106;115671 (1987).
Cummins et al., Chemical Abstracts, vol. 103:215702 (1985).
Jin, Yi, et al., "Parallel Solid-Phase Synthesis of Nucleoside Phosphoramidate Libraries," *Bioorganic & Medical Chemistry Letters*, 11: 2057-2060 (2001).
Asseline, Ulysse, et al., "Synthesis and Binding Properties of Oligonucleotides Covalently Linked to an Acridine Derivative: New Study of the Influence of the Dye Attachment Site," *Bioconjugate Chem.*, 7: 369-379 (1996).
Kumar, Prabhat, and Misra, K., "A New Strategy for the Synthesis of Phosphorothioates of 2'-Deoxyriboligonucleotides," *Indian J. of Chemistry*, 36B: 1000-1004 (1997).
Ravikumar, Vasulinga T., et al., "4-Cyano-2-Butenyl Group: A New Type of Protecting Group in Oligonucleotide Synthesis Via Phosphoramidite Approach," *Nucleosides & Nucleotides*, 16(7-9): 1709-1712 (1997).
Brill, Wolfgang K.-D., et al., "Synthesis of Oligodeoxynucleoside Phosphorodithioates via Thioamidites," *J. Am. Chem. Soc.*, 111: 2321-2322 (1989).
Agrawal, S., "Antisense Oligonucleotides as Antiviral Agents," *Trends in Biotech.*, 10(5): 152-158 (May 1992).
Mönkkönen, Jukka and Urtti, Arto, "Lipid Fusion in Oligonucleotide and Gene Delivery With Cationic Lipids," *Advanced Drug Delivery Systems*, 34(1):37-49 (1998).
Spivak, David A., and Shea, Kenneth J., "Investigation into the Scope and Limitations of Molecular Imprinting With DNA Molecules," *Analytica Chimica Acta*, 435: 65-74 (2001).
Ravikumar, Vasulinga T., et al., "Use of 2-Diphenylmethylsilylethyl (DPSE) Protecting Group on Oligonucleotide, Synthesis Via Phosphoramidite Approach," *Bioorganic & Medicinal Chem. Letters*, 3(12): 2637-2640 (1993), abstract.

* cited by examiner

*Primary Examiner*—Patrick Lewis
(74) *Attorney, Agent, or Firm*—Elmore Patent Law Group, P.C.; Darlene A. Vanstone; Carolyn S. Elmore

(57) ABSTRACT

The invention provides compounds capable of treating against hepatitis infections, particularly hepatitis B viral infections. Compounds of the invention are nucleic acid-based and preferably comprise 2, 3, 4, 5 or 6 nucleoside units.

24 Claims, No Drawings

NUCLEIC ACID-BASED COMPOUNDS AND METHODS OF USE THEREOF

RELATED APPLICATIONS

This application is a divisional of U.S. application Ser. No. 10/146,175, filed May 15, 2002 now U.S. Pat. No. 6,881,831, which claims the benefit of U.S. Provisional Application No. 60/291,471, filed on May 16, 2001. The entire teachings of the above applications are incorporated herein by reference.

FIELD OF THE INVENTION

The present invention relates to nucleic-acid based compounds. Compounds of the invention are useful for a variety of therapeutic applications, including treatment against hepatitis B virus.

BACKGROUND

Hepatitis B virus (HBV) is a compact, enveloped DNA virus belonging to the Hepadnavirus family. The virus is a major cause of chronic liver disease and hepatocellular carcinoma worldwide (Hoofnagle (1990) *N. Eng. J. Med.*, 323:337-339). HBV is associated with acute and chronic hepatitis and hepatocellular carcinoma and may be a cofactor in the development of acquired immune deficiency syndrome (Dinestag et al. in Harrison's Principles of Internal Medicine, 13$^{th}$ Ed. (Isselbacher et al. eds.) McGrw-Hill, NY, N.Y. (1993) pp. 1458-1483). At least 400 million people are currently infected with HBV.

Current clinic agents, however, do not provide effective therapy or cure of HBV infections. Antiviral therapy with interferon has been used for chronic hepatitis, but has met with only partial success, and there complications from such therapy. Short term therapy with glucocorticoids may be beneficial in conjunction with interferon therapy, but long term treatment is limited by toxicological problems (Dinestag et al., supra).

It thus would be desirable to have new agents for treatment of viral infections. It would be particularly desirable to have new agents for treatment against hepatitis B viral infections.

SUMMARY OF THE INVENTION

We have now found compounds and compositions that are particularly useful for treatment of viral infections. Preferred compounds of the invention that can exhibit significant activity against hepatitis B virus.

Compounds of the invention are nucleic-based small molecules that contain at least two nucleoside units, and typically contain no more than about 2, 3, 4, 5 or 6 nucleotide units, preferably no more than about 2, 3, or 4 nucleotide units, still more preferably a total of 2 or 3 nucleoside units. Compounds of the invention comprise at least one nucleotide unit that contains one or more modifications from "natural" nucleic acids. Preferred compounds of the invention include those that have phosphorothioate and/or phophoramidate internucleotide linkages.

Especially preferred compounds of the invention include the following compounds 1, 2 and 3, and pharmaceutically acceptable salts of such compounds:

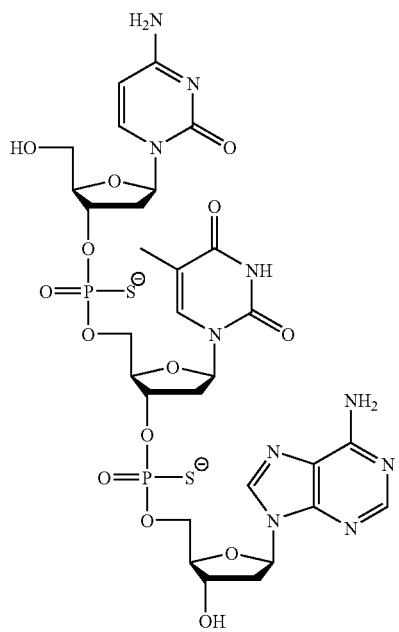

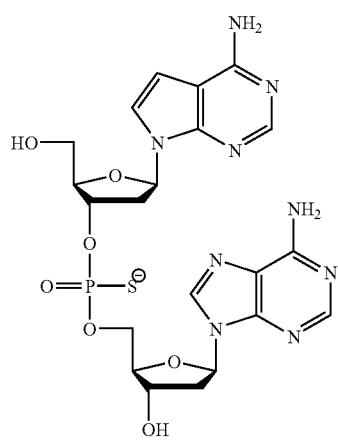

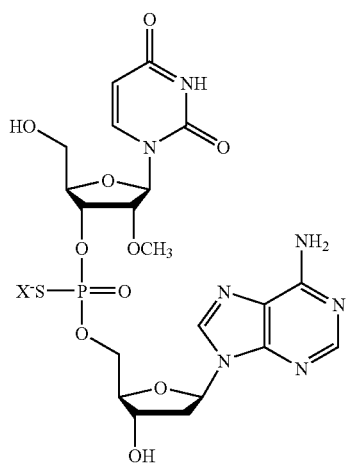

The invention also includes therapeutic methods comprising use of one or more compounds of the invention. Methods of the invention include treatment of HBV infections, including treatment and prevention (prophylactic therapy) of HBV-associated disorders or diseases.

Preferred methods of the invention include administering a therapeutic effective amount of a compound of the invention to a viral infected cell, particularly a human cell, especially a cell that is infected with HBV. Methods of the invention also comprise administering to a mammal, particularly a primate such as a human, an effective amount of one or more compounds of the invention.

The invention further provides pharmaceutical compositions that comprise one or more compound of the invention and a pharmaceutically acceptable carrier.

Other aspects of the invention are disclosed infra.

DETAILED DESCRIPTION OF THE INVENTION

As discussed above, we have discovered new synthetic oligonucleotides (at least two nucleotide units) that can exhibit significant anti-HBV activity.

Compounds of the invention comprise one or more modifications from "natural" nucleic acids, i.e. natural internucleoside linkages, bases of G, C, T and U, etc. Modifications include, for example, modifications of the internucleotide linkage, the base or the sugar moiety, etc.

Compounds of the invention suitably contain two or more deoxyribonucleotide and/or ribonucleotide monomers connected by internucleotide linkages. Compounds of the invention may be constructed entirely of deoxyribonucleotides, entirely of ribonucleotides or of a combination of deoxyribonucleotides and ribonucleotides, including hybrid and inverted hybrid compounds. Hybrid compounds contain a core region (e.g. 1, 2 or 3 units) of deoxyribonucleotides interposed between flanking regions of ribonucleotides (e.g. 1, 2 or 3 units). Inverted hybrids contain a core region of ribonucleotides (e.g. 1, 2, or 3 units) interposed between flanking regions of deoxyribonucleotides (e.g. 1, 2 or 3 units).

Nucleotide units of compounds of the invention may be connected by standard phosphodiester internucleotide linkages between the 5' group of one mononucleotide pentose ring and the 3' group of an adjacent mononucleotide. Such linkages could also be established using different sites of connection, including 5' to 5', 3' to 3', 2' to 5' and 2' to 2', or any combination thereof. In addition to phosphodiester linkages, the mononucleotides may also be connected by alkylphosphonate, phosphorothioate, phosphorodithioate, alkylphosphonothioate, phosphoramidate, carbamate, carbonate, phosphate triester, acetamidate, or carboxymethyl ester linkages, or any combination thereof. As discussed above, preferred compounds of the invention include at least one phosphorothioate and/or phosphoramidate linkage.

Compounds of the invention may be constructed such that all mononucleotides units (e.g. 2, 3, 4, 5 or 6 total units) are connected by the same type of internucleotide linkages or by combinations of different internucleotide linkages, including chimeric or inverted chimeric oligonucleotides. Chimeric compounds of the invention have a phosphorothioate core region interposed between methylphosphonate or phosphoramidate flanking regions. Inverted chimeric compounds of the invention have a nonionic core region (e.g. alkylphosphonate and/or phosphoramidate and/or phosphotriester internucleoside linkage) interposed between phosphorothioate flanking regions.

Compounds of the invention also may be constructed of adenine, cytosine, guanine, inosine, thymidine or uracil mononucleotides. Preferred compounds of the invention may be constructed from mononucleotide units which contain modifications to the base and/or sugar moiety of the mononucleotide. Modifications to the base or sugar include covalently attached substituents of alkyl, carbocyclic aryl, heteroaromatic or heteroalicyclic groups having from 1 to 3 separate or fused rings and 1 to 3 N, O or S atoms, or a heterocyclic structure.

Alkyl groups preferably contain from 1 to about 18 carbon atoms, more preferably from 1 to about 12 carbon atoms and most preferably from 1 to about 6 carbon atoms. Specific examples of alkyl groups include, for example, methyl, ethyl, n-propyl, isopropyl, n-butyl, t-butyl, isobutyl, pentyl, hexyl, heptyl, octyl, nonyl, decyl etc. Aralkyl groups include the above-listed alkyl groups substituted by a carbocyclic aryl group having 6 or more carbons, for example, phenyl, naphthyl, phenanthryl, anthracyl, etc.

Cycloalkyl groups preferably have from 3 to about 8 ring carbon atoms, e.g. cyclopropyl, cyclopentyl, cyclohexyl, cycloheptyl, 1,4-methylenecyclohexane, adamantyl, cyclopentylmethyl, cyclohexylmethyl, 1- or 2-cyclohexylethyl and 1-, 2- or 3-cyclohexylpropyl, etc.

Exemplary heteroaromatic and heteroalicyclic group include pyridyl, pyrazinyl, pyrimidyl, furyl, pyrrolyl, thienyl, thiazolyl, oxazolyl, imidazolyl, indolyl, benzothiazolyl, tetrahydrofuranyl, tetrahydropyranyl, piperidinyl, morpholino and pyrrolidinyl.

Preferred modifications to the sugar group include modifications to the 2' position of the ribose moiety which include but are not limited to 2'—O-substituted with an —O-lower alkyl group containing 1-6 saturated or unsaturated carbon atoms, or with an —O-aryl, or allyl group having 2-6 carbon atoms wherein such —O-alkyl, aryl or allyl group may be unsubstituted or may be substituted (e.g., with halogen, hydroxy, trifluoromethyl, cyano, nitro, acyl, acyloxy, alkoxy, carboxy, carbalkoxyl, or amino groups), or wherein the 2'—O-group is substituted by an amino, or halogen group. None of these substitutions are intended to exclude the native 2'-hydroxyl group in case of ribose or 2'—H— in the case of deoxyribose.

Preferred compounds of the invention having modified nucleotide units include 2'—O-methyl ribonucleotides (2'—OMe) and 5-methylated deoxycytosine (5-Me-dC). Particularly preferred compounds of the invention comprises at least one, preferably one to five 2'—O-methyl ribonucleotides at the 3' end of the oligonucleotide. Moreover, a compound of the invention may further comprise at least one, preferably one to five 2'—O-methyl ribonucleotides at the 5'-end.

Sugar groups of mononucleotide units of compounds of the invention may be natural or modified (e.g. synthetic) and in an open chain or ring form. Sugar groups may be comprised of mono-, di-, oligo- or poly-saccharides wherein each monosaccharide unit comprises from 3 to about 8 carbons, preferably from 3 to about 6 carbons, containing polyhydroxy groups or polyhydroxy and amino groups. Non-limiting examples include glycerol, ribose, fructose, glucose, glucosamine, mannose, galactose, maltose, cellobiose, sucrose, starch, amylose, amylopectin, glycogen and cellulose. The hydroxyl and amino groups are present as free or protected groups containing e.g. hydrogens and/or halogens. Preferred protecting groups include acetonide, t-butoxy carbonyl groups, etc. Monosaccharide sugar groups may be of the L or D configuration and a cyclic monosaccharide unit may contain a 5 or 6 membered ring of the α or β conformation. Disaccharides may be comprised of two identical or two dissimilar monosaccharide units. Oligosaccharides may be comprised of from 2 to 10 monosaccharides and may be homopolymers, heteropolymers or cyclic polysugars. Polysaccharides may be homoglycans or heteroglycans and may be branched or unbranched polymeric chains.

The di-, oligo- and poly-saccharides may be comprised of 1⇒4, 1⇒6 or a mixture of 1⇒4 and 1⇒6 linkages. The sugar moiety may be attached to the link group through any of the hydroxyl or amino groups of the carbohydrate.

Other modifications include those which are internal or are at the end(s) of a compound of the invention and include additions to the molecule at the internucleoside phosphate linkages, such as cholesterol, cholesterol or diamine compounds with varying numbers of carbon residues between the two amino groups, and terminal ribose, deoxyribose and phosphate modifications which cleave, or crosslink to the opposite chains or to associated enzymes or other proteins which bind to the viral genome. Additional linkers including non-nucleoside linkers include, but are not limited to, polyethylene glycol of varying lengths, e.g., triethylene glycol, monoethylene glycol, hexaethylene glycol, (Ma et al. (1993) *Nucleic Acids Res.* 21: 2585-2589; Benseler et al. (1993) *J. Am. Chem. Soc.* 115: 8483-8484), hexylamine, and stilbene (Letsinger et al, (1995) *J. Am. Chem. Soc.* 117: 7323-7328) or any other commercially available linker including abasic linkers or commercially available asymmetric and symmetric linkers (CloneTech, Palo Alto, Calif.) (e.g., Glen Research Product Catalog, Sterling, Va.).

Additionally compounds of the invention capped with ribose at the 3' end of the oligonucleotide may be subjected to $NaIO_4$ oxidation/reductive amination. Amination may include but is not limited to the following moieties, spermine, spermidine, Tris(2-aminoethyl) amine (TAEA), DOPE, long chain alkyl amines, crownethers, coenzyme A, NAD, sugars, peptides, dendrimers.

Compounds of the invention also may be capped with a bulky substituent at their 3' and/or 5' end(s), or have a substitution in one or both nonbridging oxygens per nucleotide. Such modifications can be at some or all of the internucleoside linkages, as well as at either or both ends of the oligonucleotide and/or in the interior of the molecule (reviewed in Agrawal et al. (1992) *Trends Biotechnol.* 10: 152-158). Some non-limited examples of capped species include 3'—O-methyl, 5'—O-methyl, 2'—O-methyl, and any combination thereof.

Specifically preferred compounds of the invention include the following compounds 1 through 62:

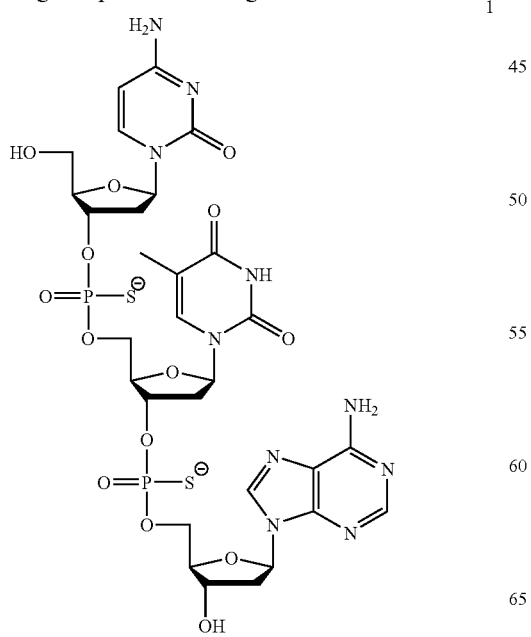

1

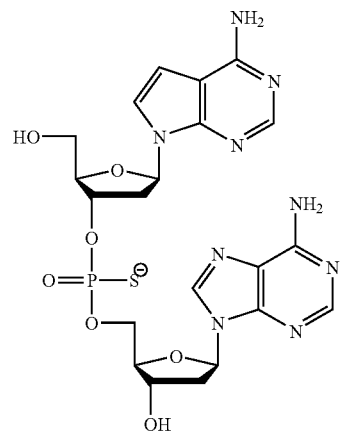

2

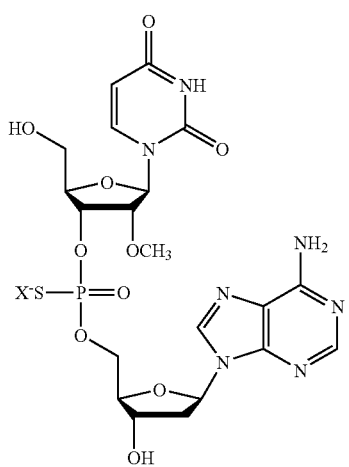

3

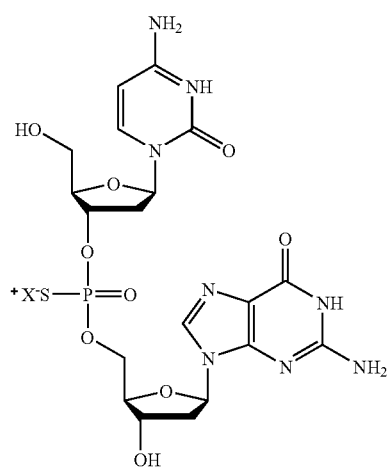

4

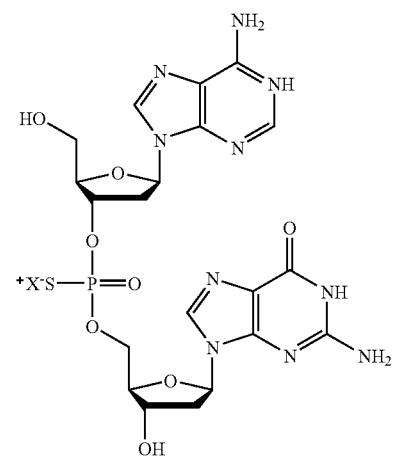
5
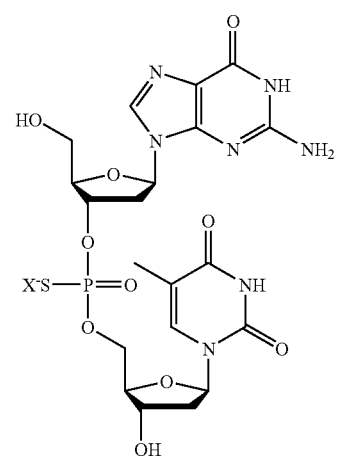
6
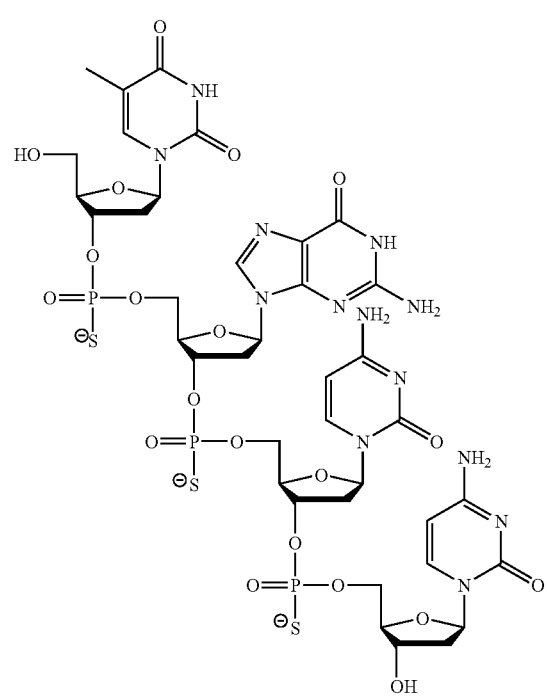
7
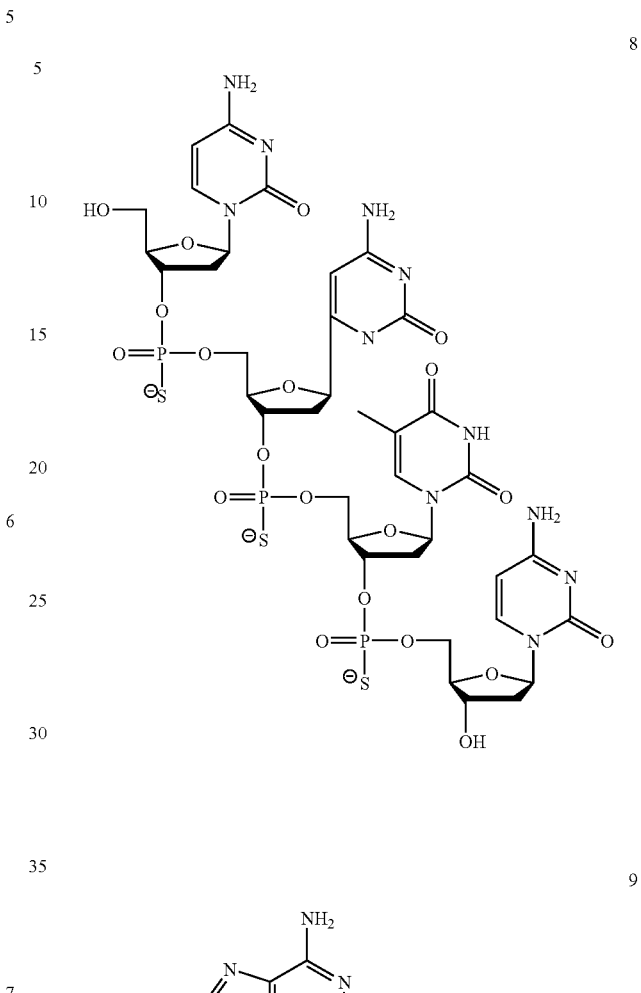
8
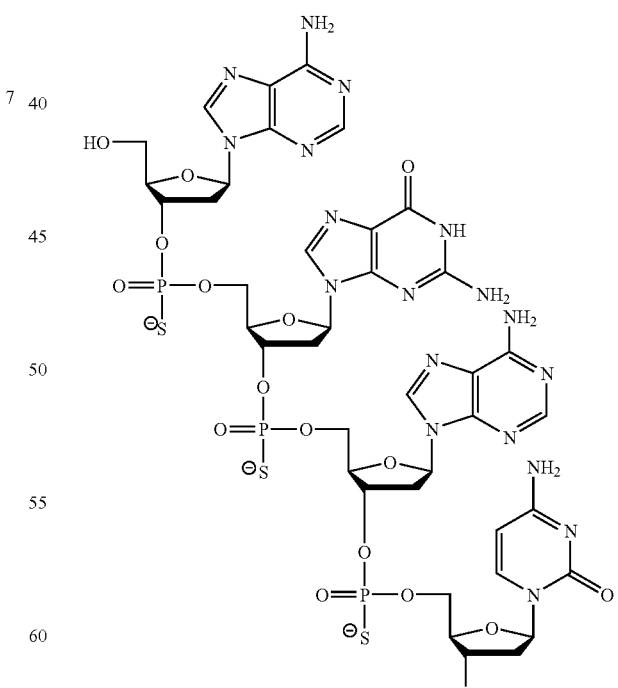
9

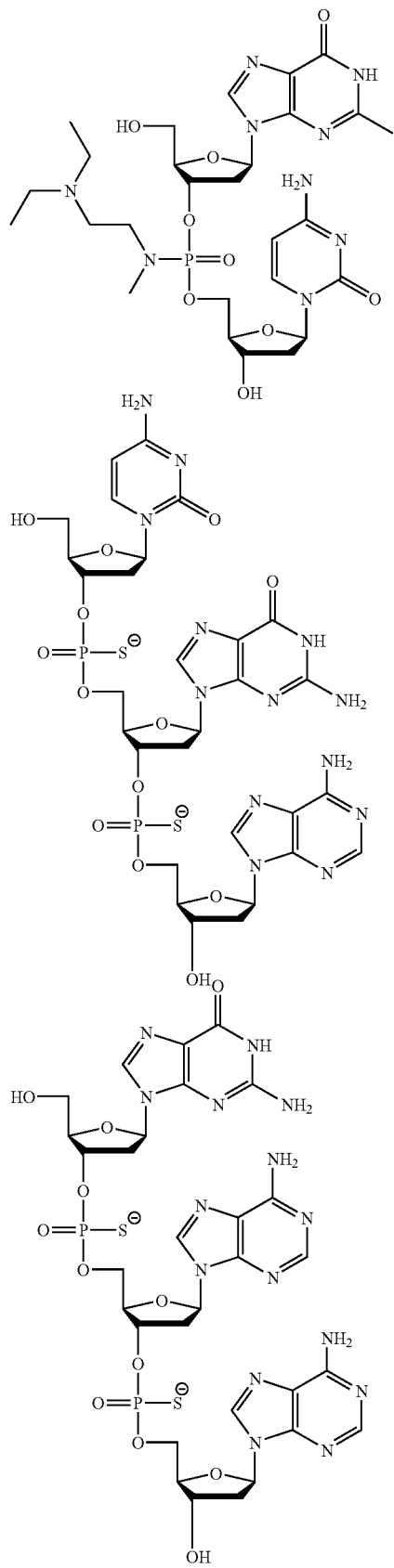
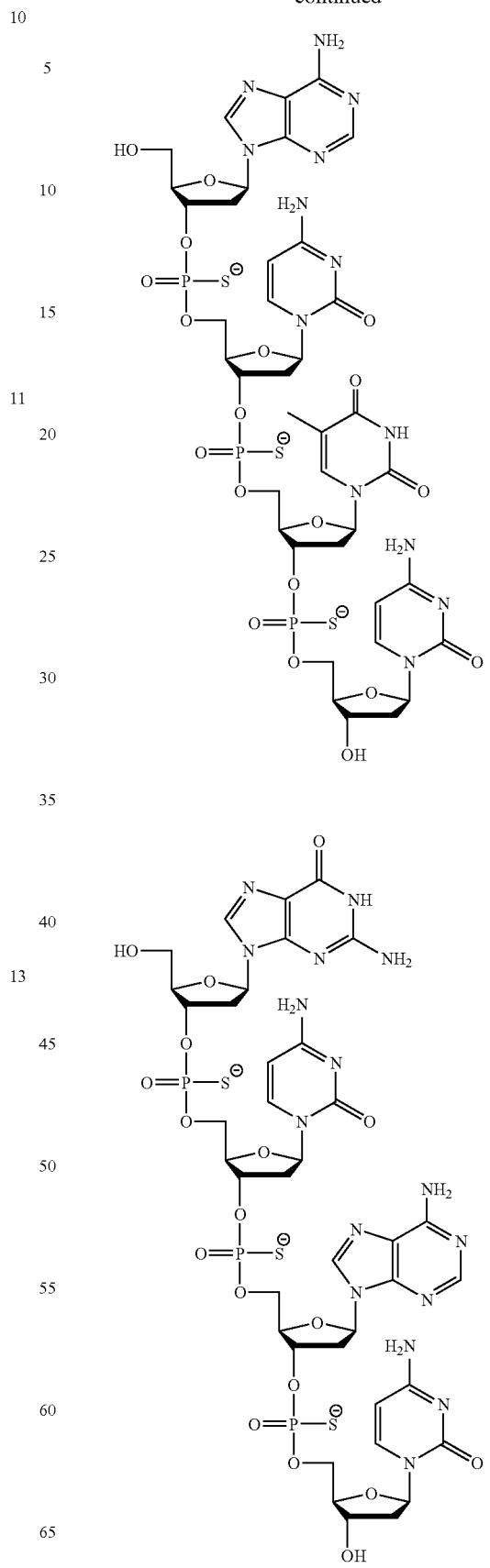

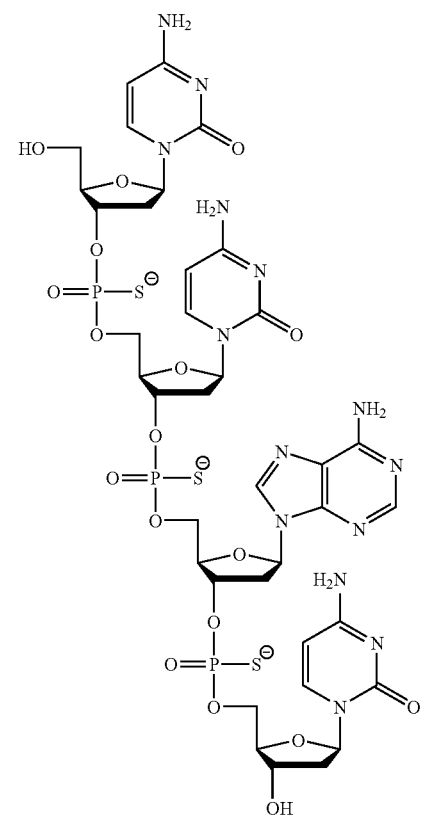
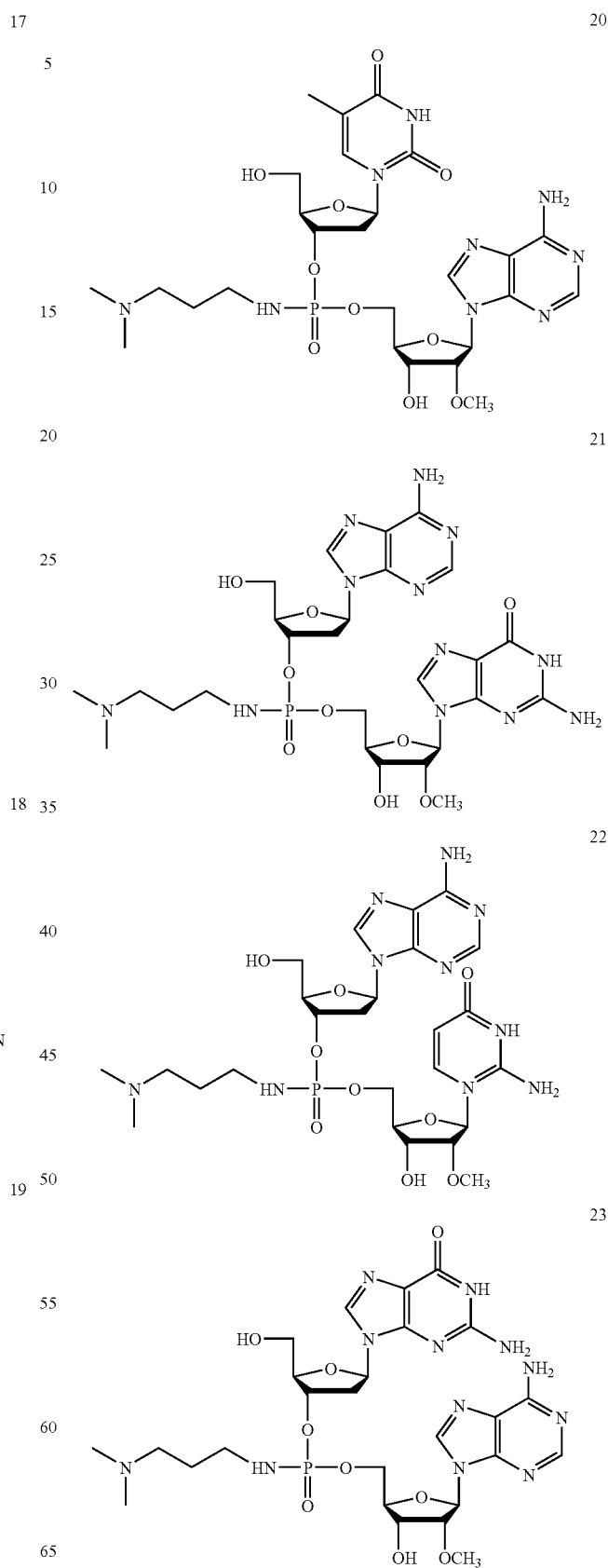

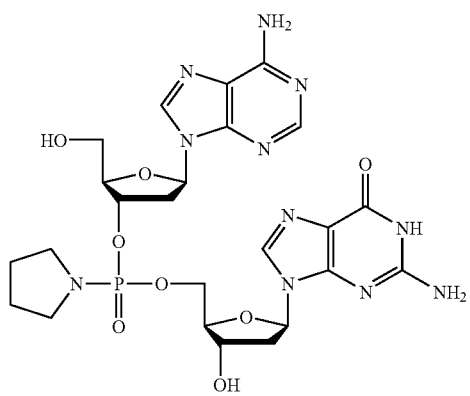
24
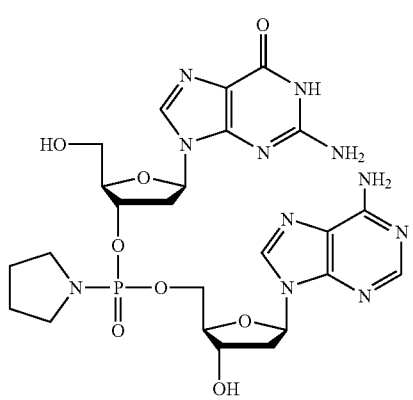
28
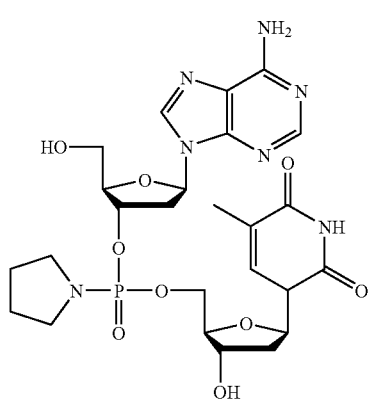
25
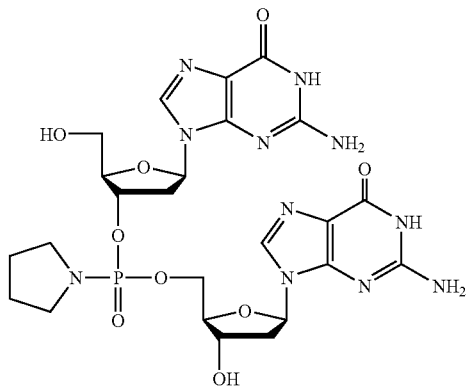
29
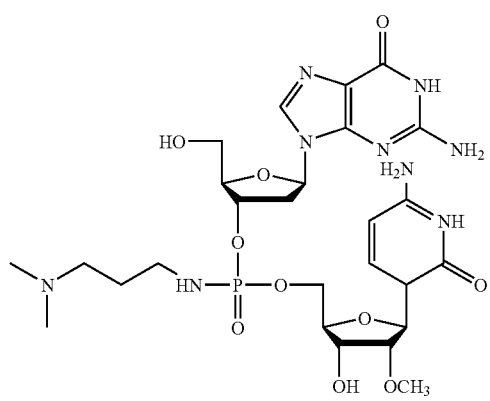
26
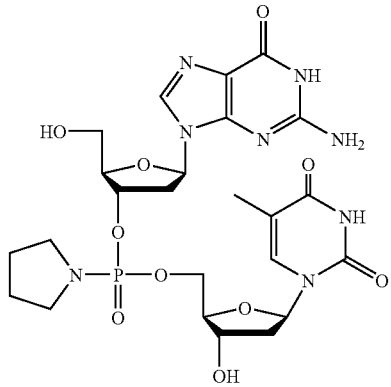
30
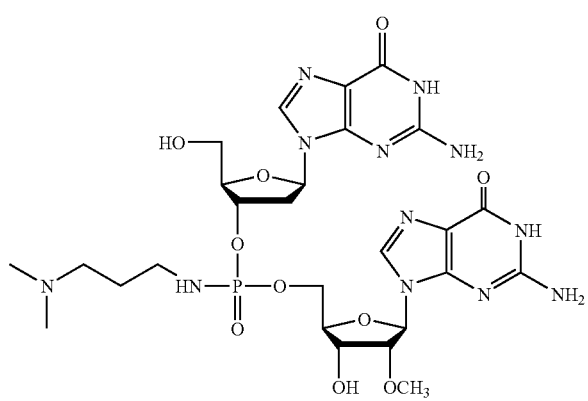
27
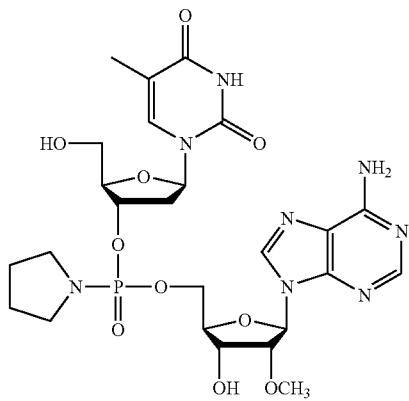
31

32
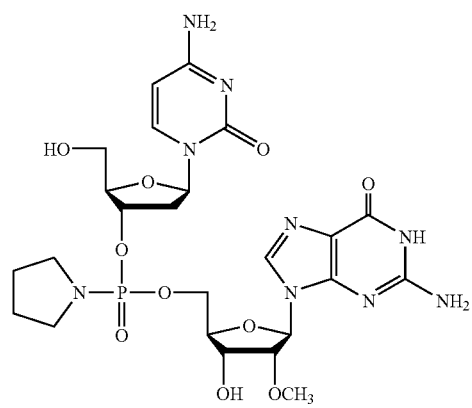
33
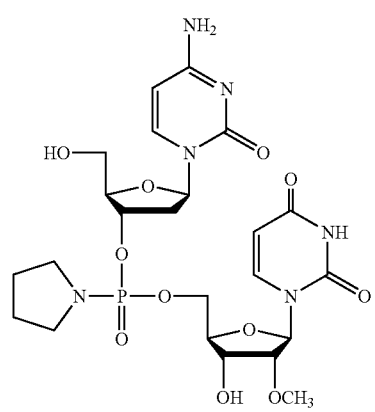
34
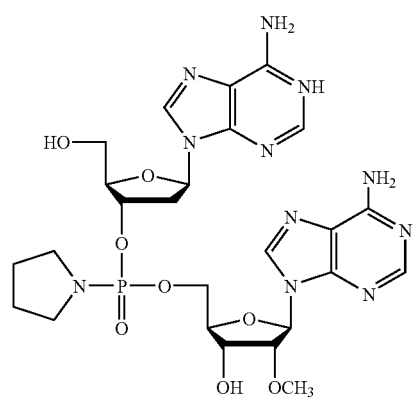
35
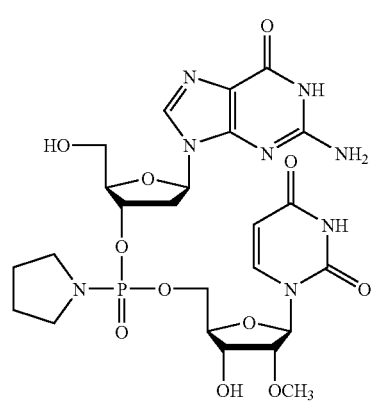
36
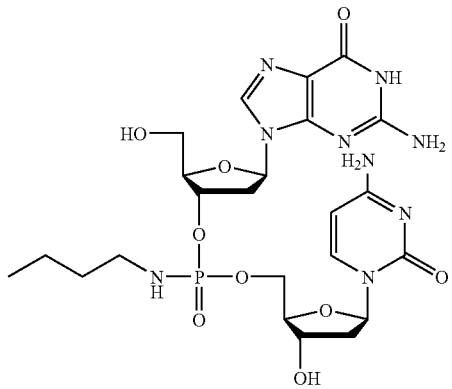
37
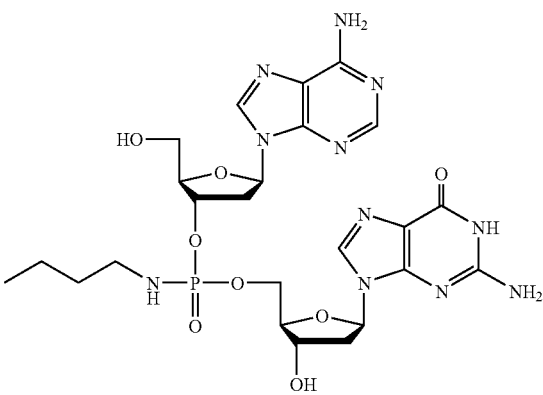
38
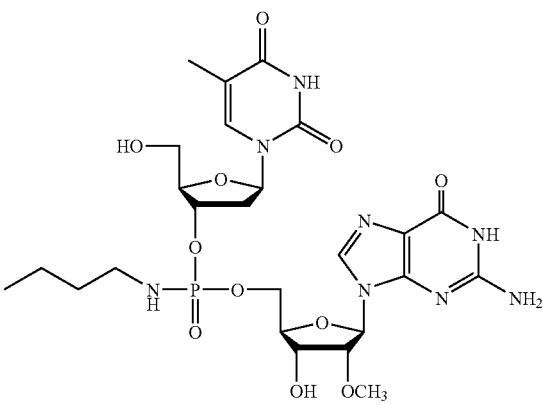
39
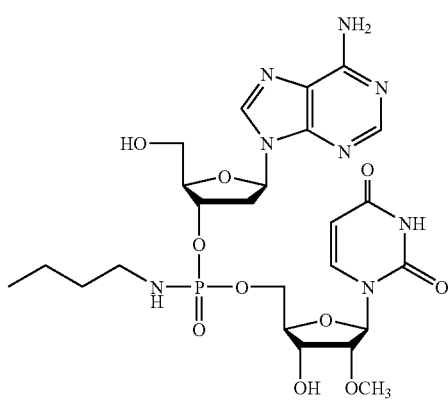

-continued
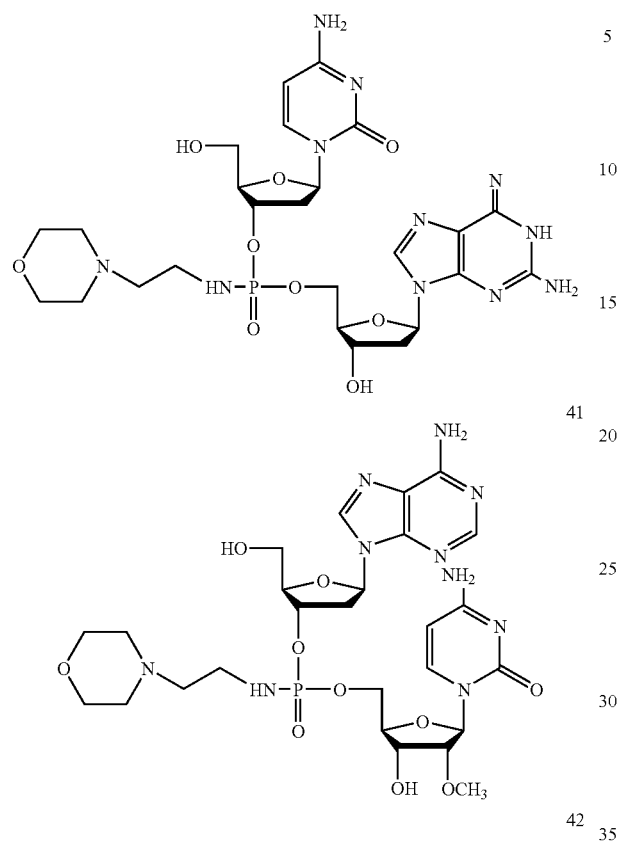
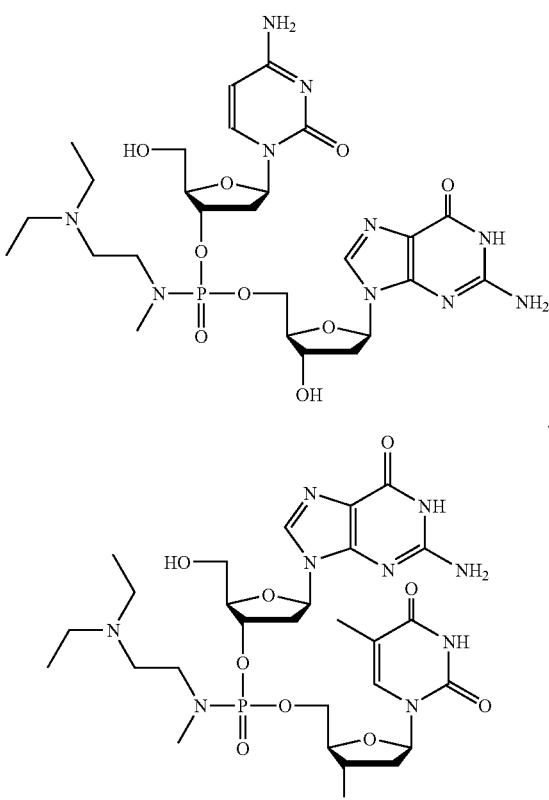
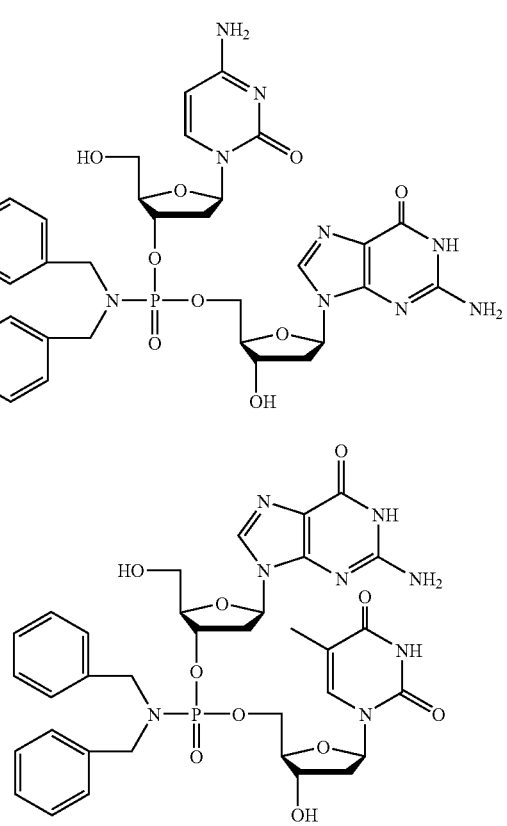

48
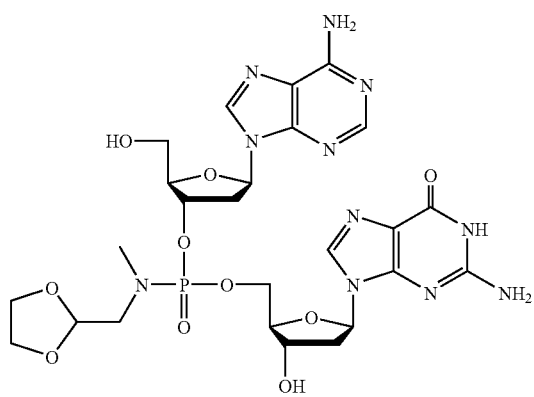
49
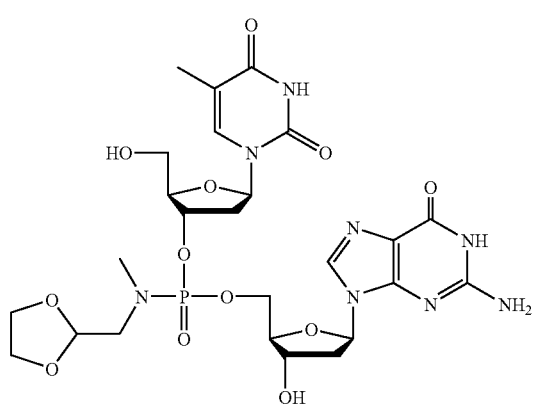
50
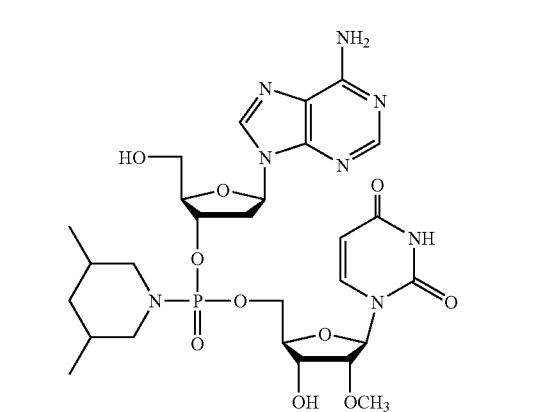
51
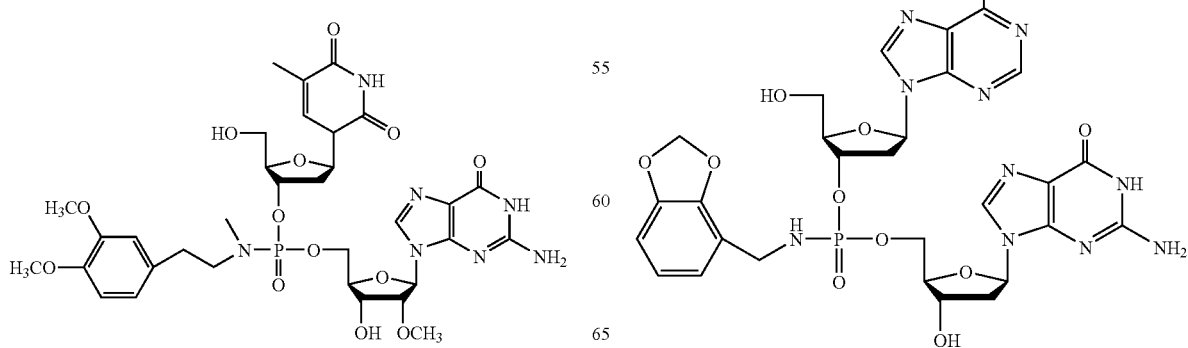
52
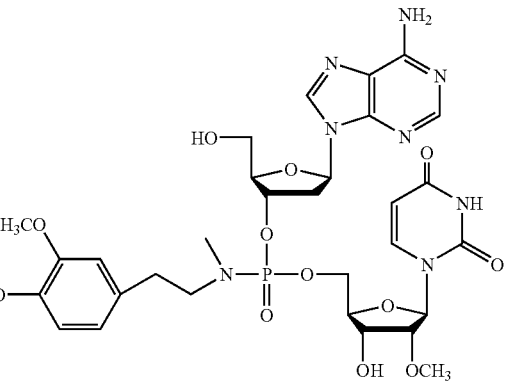
53
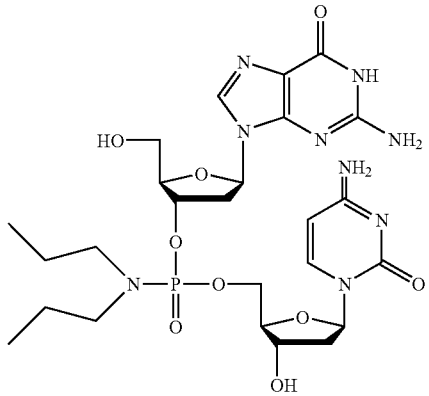
54
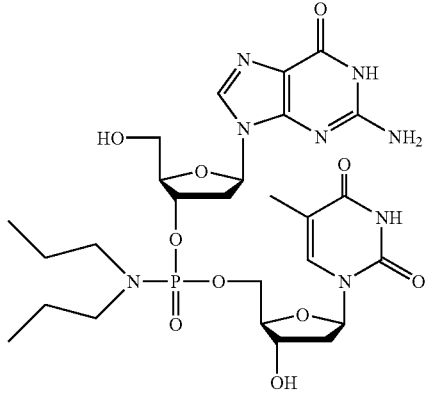
55
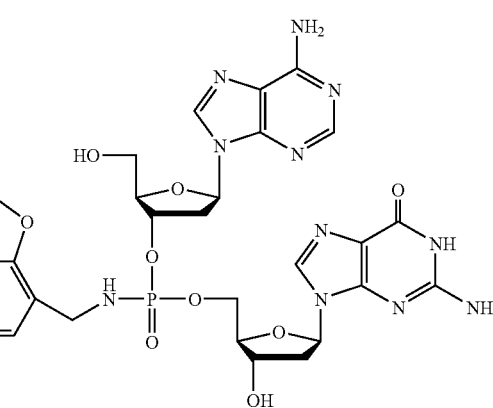

56
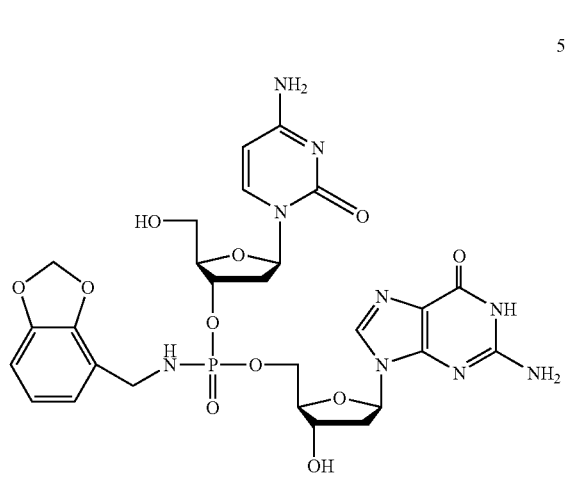
57
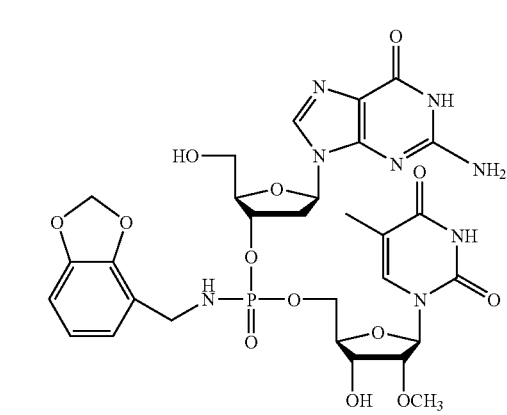
58
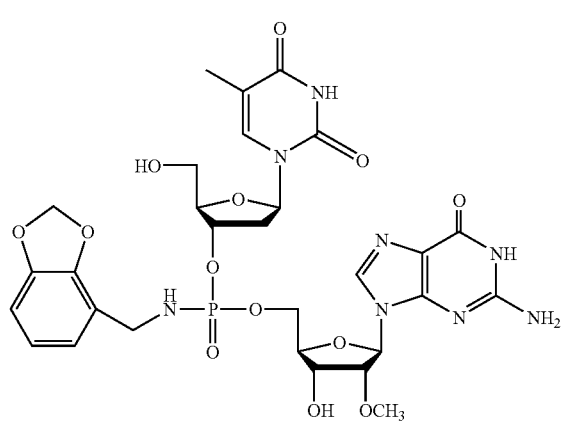
59
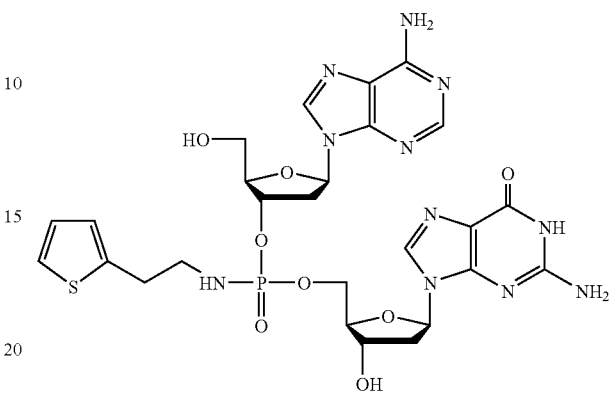
60
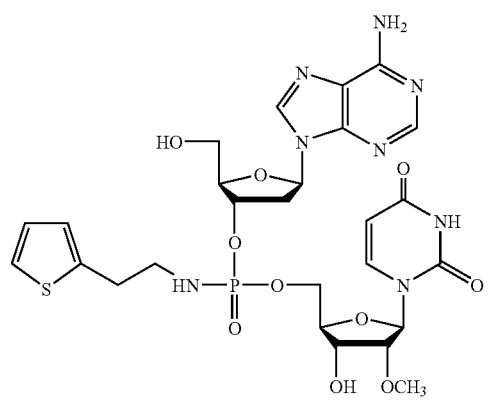
61
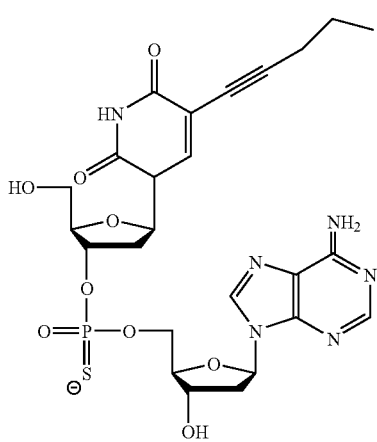

-continued

62

Compounds of the can be prepared by art recognized methods. For example, nucleotide units can be covalently linked using art-recognized techniques such as phosphoramidite, H-phosphonate chemistry, or methylphosphoramidite chemistry (see, e.g., Goodchild (1990) *Bioconjugate Chem.* 2: 165-187; Uhlmann et al. (1990) *Chem. Rev.* 90: 543-584; Caruthers et al. (1987) *Meth. Enzymol.* 154: 287-313; U.S. Pat. No. 5,149,798) which can be carried out manually or by an automated synthesizer and then processed (reviewed in Agrawal et al. (1992) *Trends Biotechnol.* 10: 152-158). Compounds of the invention with phosphorothioate linkages can be prepared using methods well known in the field such as phosphoramidite (see, e.g., Agrawal et al. (1988) *Proc. Natl. Acad. Sci.* (USA) 85: 7079-7083) or H-phosphonate (see, e.g., Froehler (1986) *Tetrahedron Lett.* 27: 5575-5578) chemistry. The synthetic methods described in Bergot et al. (*J. Chromatog.* (1992) 559: 35-42) can also be used. Oligonucleotides with other types of modified internucleotide linkages can be prepared according to known methods (see, e.g., Goodchild (1990) *Bioconjugate Chem.* 2: 165-187; Agrawal et al. (1988) *Proc. Natl. Acad. Sci.* (USA) 85: 7079-7083; Uhlmann et al. (1990) *Chem. Rev.* 90: 534-583; and Agrawal et al. (1992) *Trends Biotechnol.* 10: 152-158).

As discussed above, the invention provides a pharmaceutical composition which comprises at least one compound of the invention, preferably together with a pharmaceutically acceptable carrier. Specific embodiments include a therapeutic amount of a lipid carrier.

As discussed above, compounds of the invention are suitable for use in a variety of therapeutic application, particularly to treat against a viral infection in mammalian cells, particularly human cells. Compounds of the invention are especially for use in the control or prevention of hepatitis viruses, particularly control or prevention of hepatitis B viral infections in human cells.

Compounds of the invention also are useful to treat against drug-resistant viral strains, including strains of hepatitis B virus that are resistant to current therapies.

Preferred therapeutic methods of the invention include administering a therapeutic amount of a pharmaceutical composition containing one or more compounds of the invention to a cell to thereby inhibit or otherwise treat against a hepatitis B viral infection. In a similar aspect, compounds of the invention can be used for treating hepatitis B viral infections comprising the step of administering to an infected cell or animal, particularly a primate such as a human, a therapeutic amount of a pharmaceutical composition containing at least one compounds of the invention.

Compounds of the invention may be used in therapy in conjunction with other medicaments such as reverse transcriptase inhibitors such as a dideoxynucleoside e.g. 3TC.

Also preferred is administration of multiple, distinct compounds of the invention to a subject as part of a coordinated therapeutic regime. Particularly preferred is where at least two or more preferably all three of compounds 1, 2 and 3 are administered to a patient as part of a coordinated administration regime.

Such combination therapy, i.e. of a compound of the invention either with a distinct agent such as 3Tc, or with an additional compound of the invention may be accomplished by administration of the same or different pharmaceutical formulations, or sequential administration of the distinct agents. Generally preferred however is the substantially simultaneous of multiple distinct agents to a patient, e.g. in a unitary pharmaceutical composition containing the compounds.

Administration of compounds of the invention may be made by a variety of suitable routes including oral, topical (including transdermal, buccal or sublingual), nasal and parenteral (including intraperitoneal, subcutaneous, intravenous, intradermal or intramuscular injection) with oral or parenteral being generally preferred. It also will be appreciated that the preferred method of administration and dosage amount may vary with, for example, the condition and age of the recipient.

Compounds of the invention may be used in therapy in conjunction with other pharmaceutically active medicaments, such as another anti-viral agent, or an anti-cancer agent. Additionally, while one or more compounds of the invention may be administered alone, they also may be present as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Therapeutic compounds of the invention also may be incorporated into liposomes. The incorporation can be carried out according to known liposome preparation procedures, e.g. sonication and extrusion. Suitable conventional methods of liposome preparation are also disclosed in e.g. A. D. Bangham et al., *J. Mol. Biol.*, 23: 238-252 (1965); F. Olson et al., *Biochim. Biophys. Acta*, 557: 9-23 (1979); F. Szoka et al., *Proc. Nat. Acad. Sci.*, 75:4194-4198 (1978); S. Kim et al., *Biochim. Biophys. Acta*, 728: 339-348 (1983); and Mayer et al., *Biochim. Biophys. Acta*, 858: 161-168 (1986).

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests.

All documents mentioned herein are incorporated herein by reference.

The present invention is further illustrated by the following examples. These examples are provided to aid in the understanding of the invention and are not to be construed as limitations thereof.

EXAMPLE 1

Synthesis of Compounds of the Invention

Compounds of the invention can be synthesized using standard phosphoramidite chemistry (Beaucage (1993) *Meth. Mol. Biol.* 20: 33-61) on either an ABI 394 DNA/RNA synthesizer (Perkin-Elmer, Foster City, Calif.), a Pharmacia Gene Assembler Plus (Pharmacia, Uppsala, Sweden) or a Gene Assembler Special (Pharmacia, Uppsala, Sweden) using the manufacturers' standard protocols and custom methods.

EXAMPLE 2

Biological Testing

HBV-infected human cells (2.2.15 cells) infected were treated (in vitro) with compounds of the invention. Significant depressions (greater than 2-fold relative to the control) in extracellular (virion) HBV DNA levels produced by the cells were observed for the above compounds, including compounds 1, 2 and 3.

The invention has been described in detail with reference to preferred embodiments thereof. However, it will be appreciated that those skilled in the art, upon consideration of this disclosure, may make modifications and improvements within the spirit and scope of the invention as set forth in the following claims.

What is claimed is:

1. A compound having the structure of any one of compounds 1, 2, 4, 7-11, 13, 14 or 16-62, or a pharmaceutically acceptable salt thereof, wherein compounds 1, 2, 4, 7-11, 13, 14, and 16-62 have the following structures:

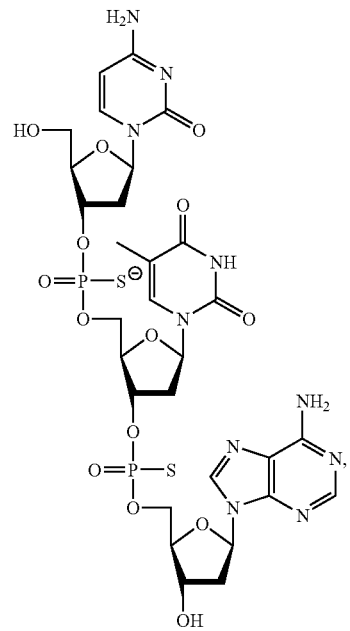

(1)

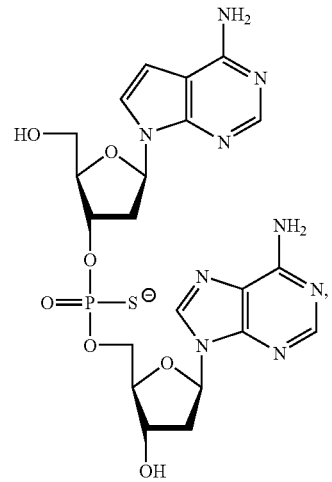

(2)

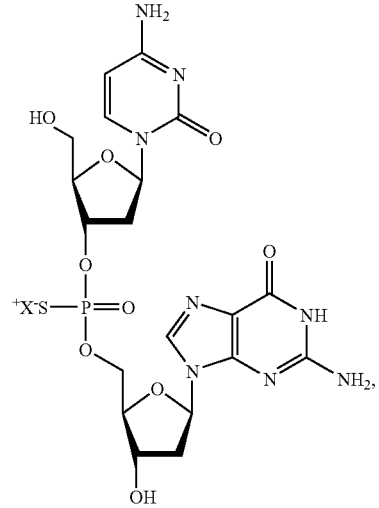

(4)

(7)
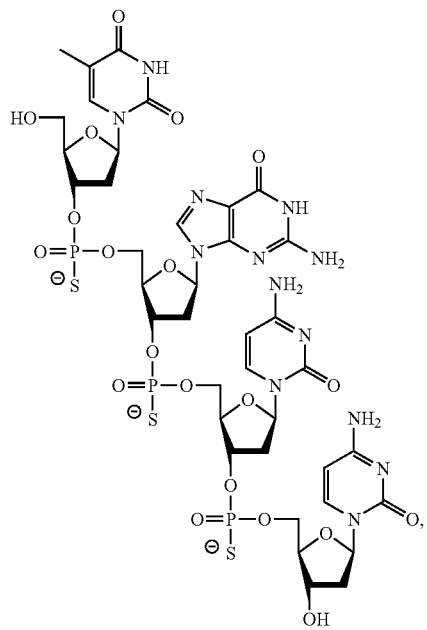
(8)
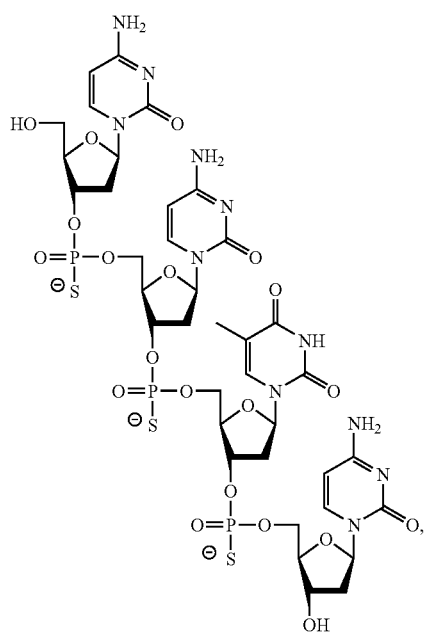
(9)
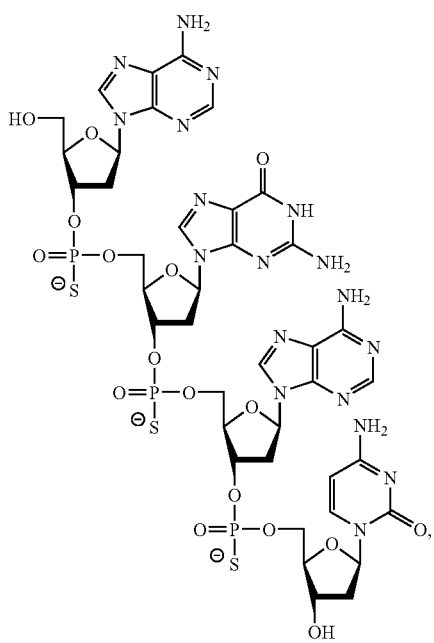
(10)
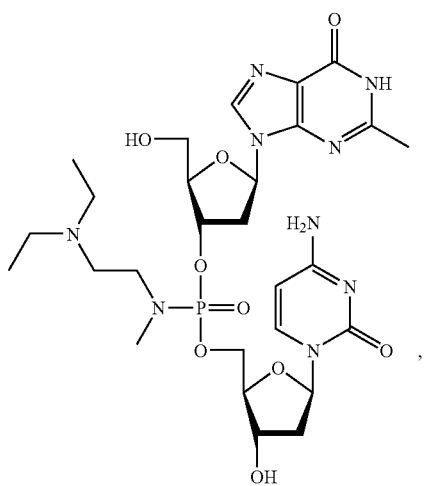

-continued
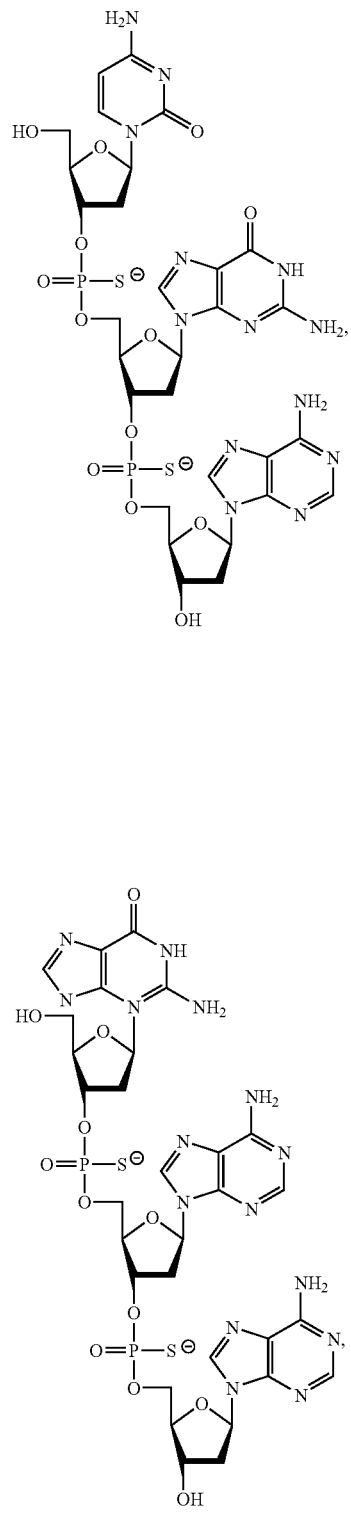
(11)
(13)
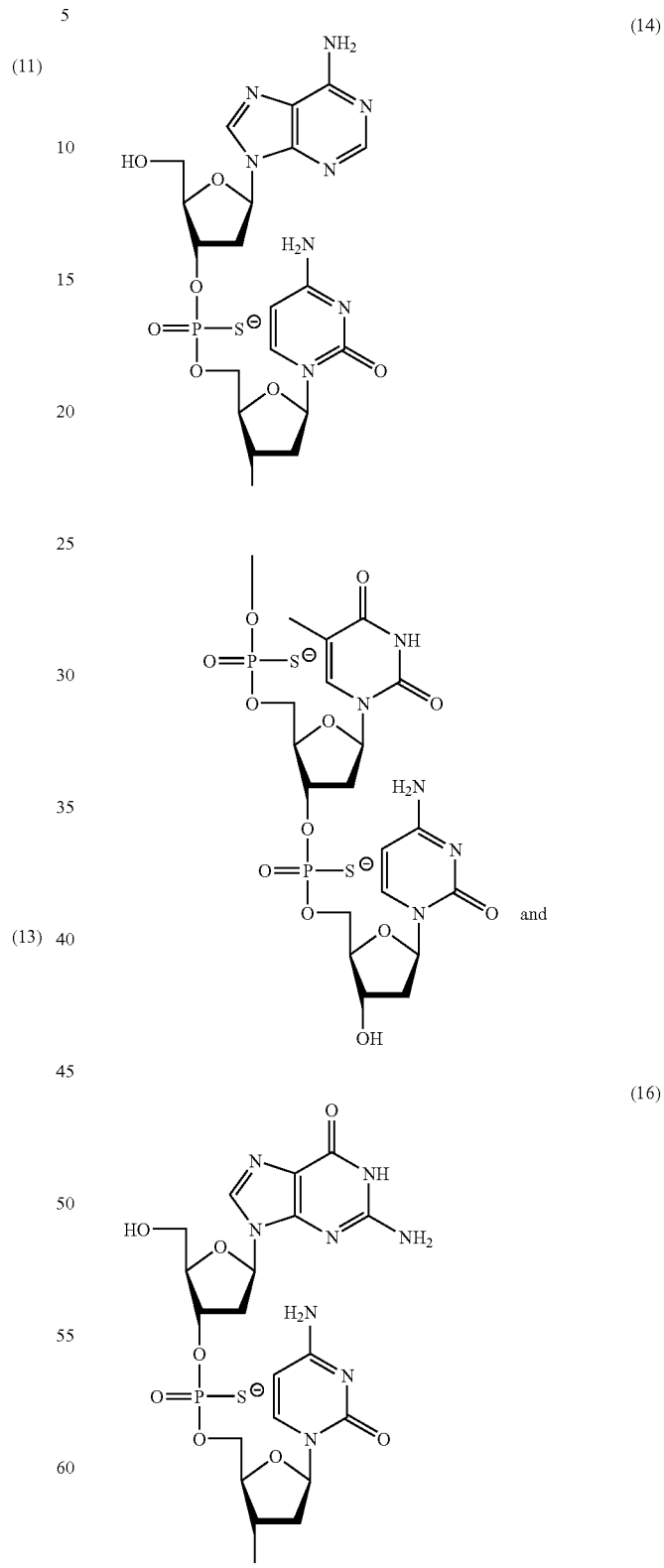
(14)
and
(16)

-continued
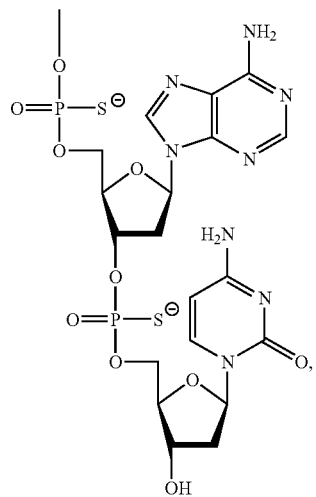
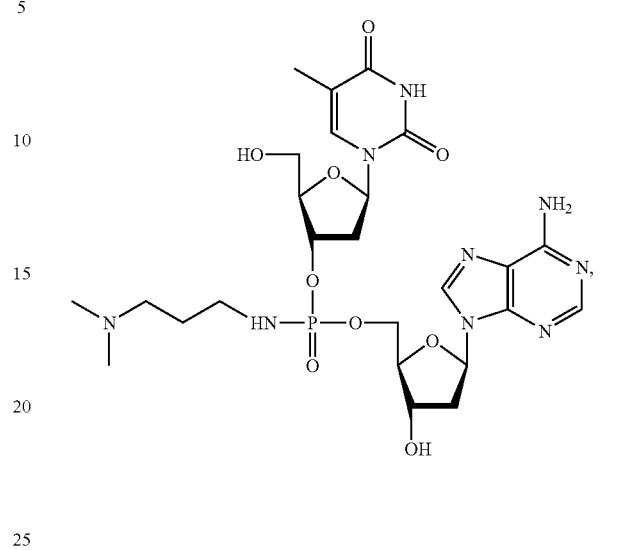
(18)
(17)
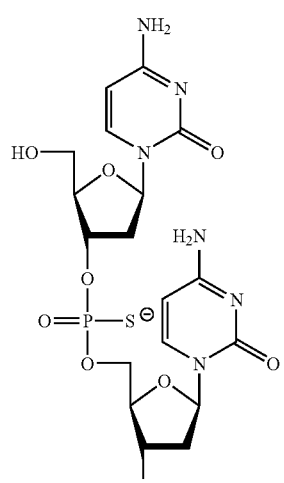
(19)
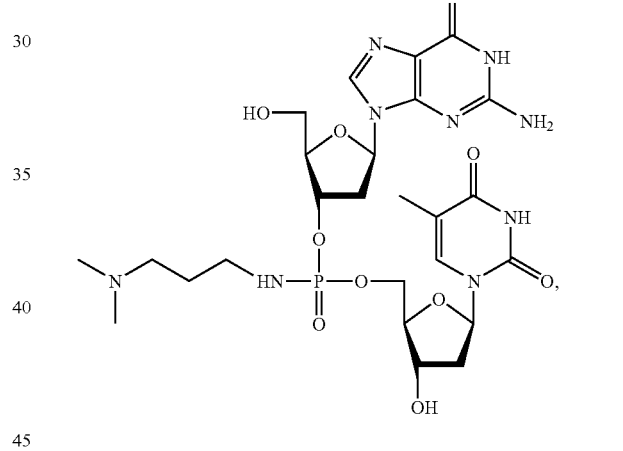
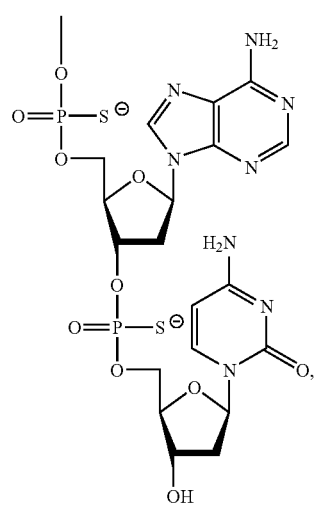
(20)
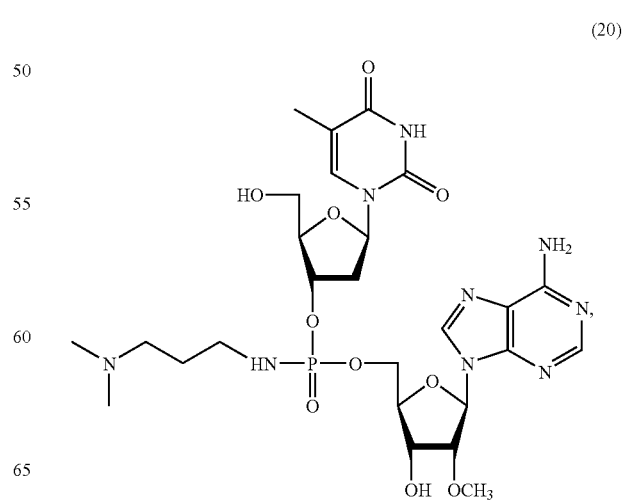

(21) (24) (22) (25) (23) (26)

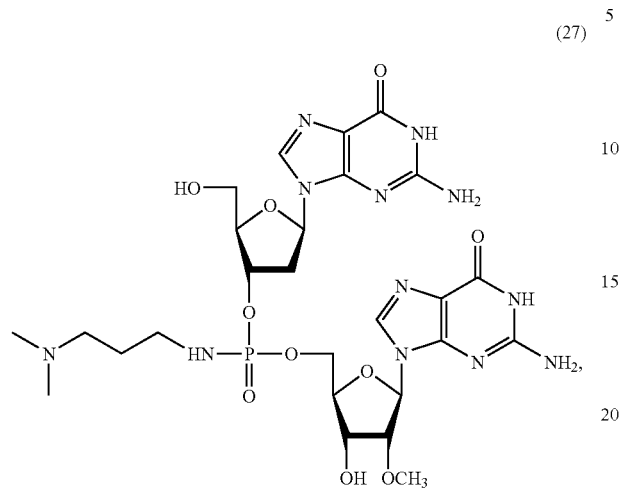
(27)
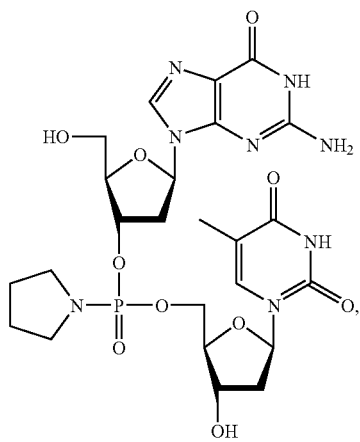
(30)
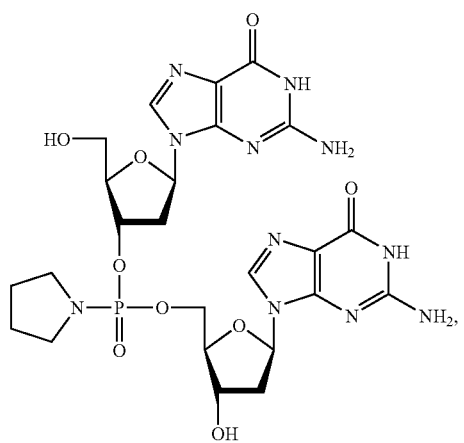
(28)
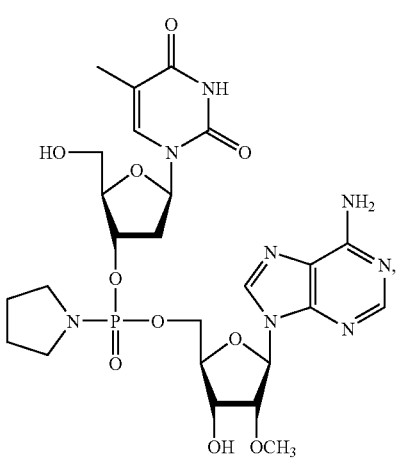
(31)
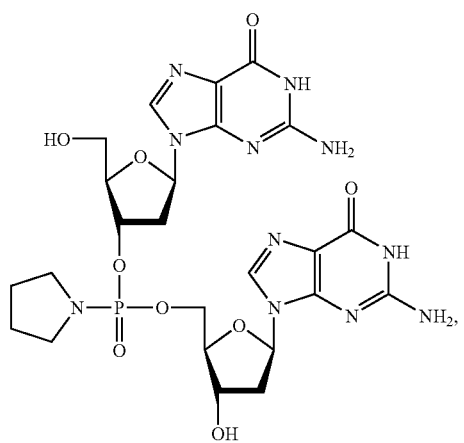
(29)
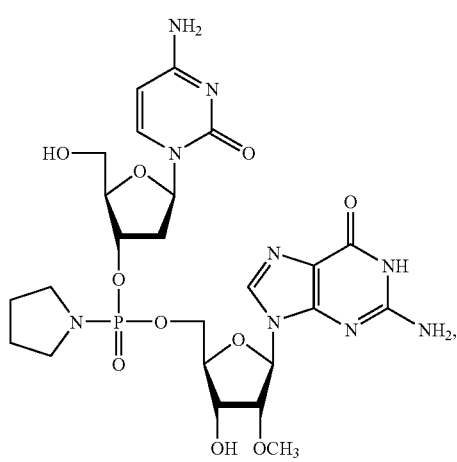
(32)

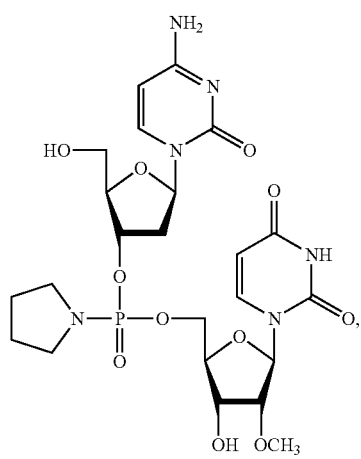
(33)
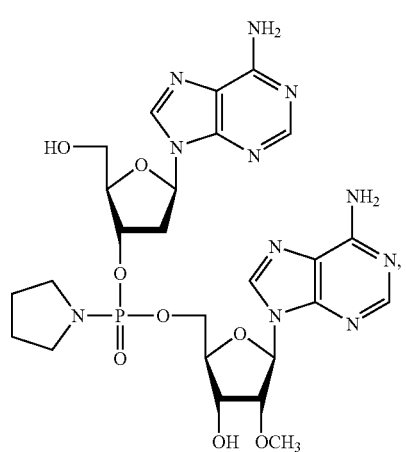
(34)
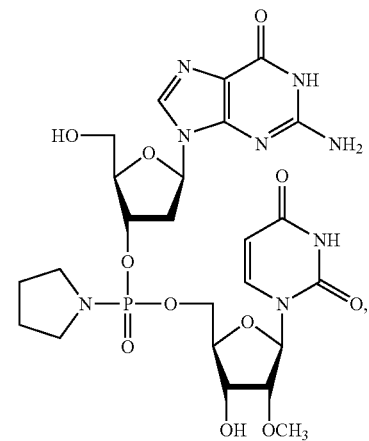
(35)
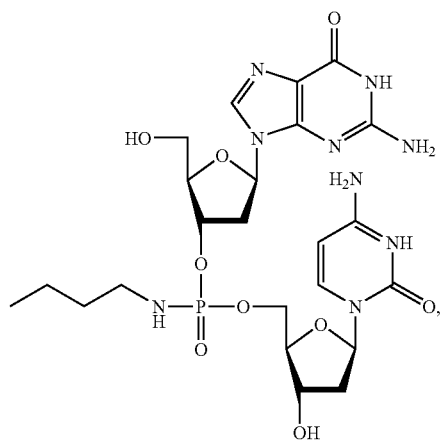
(36)
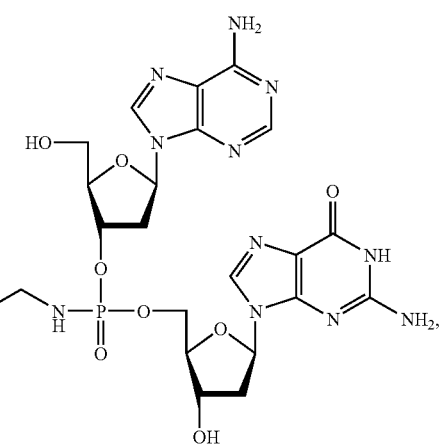
(37)
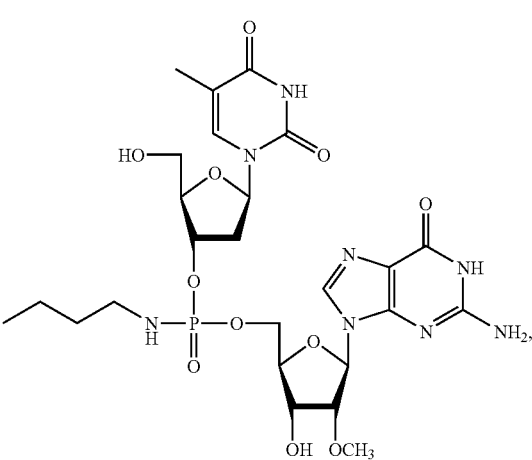
(38)

-continued
(39)
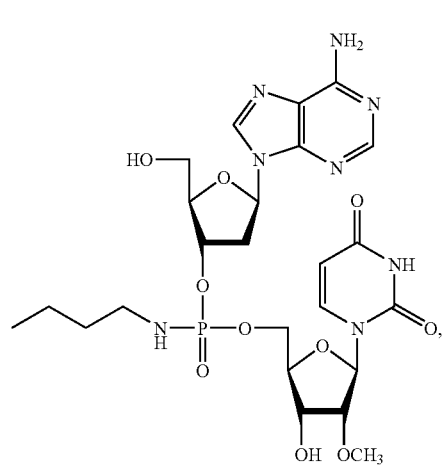
(40)
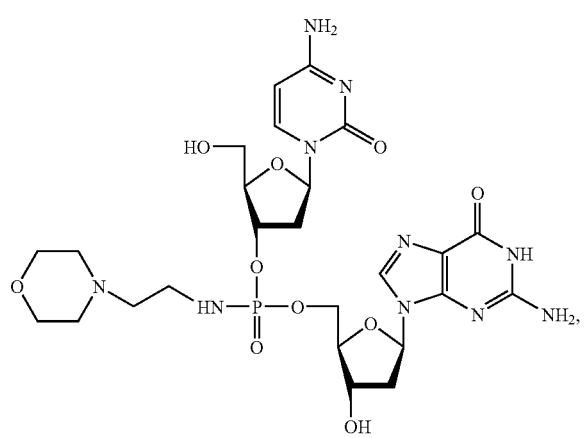
(41)
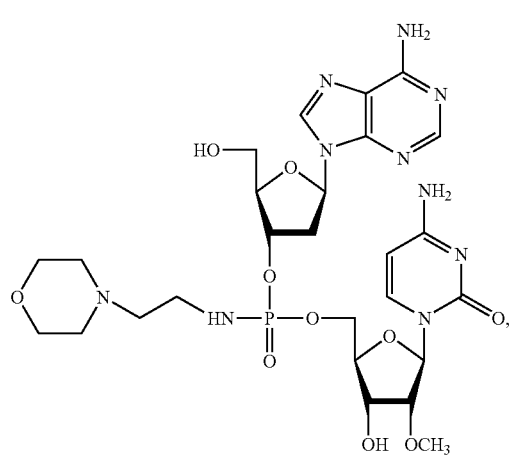
-continued
(42)
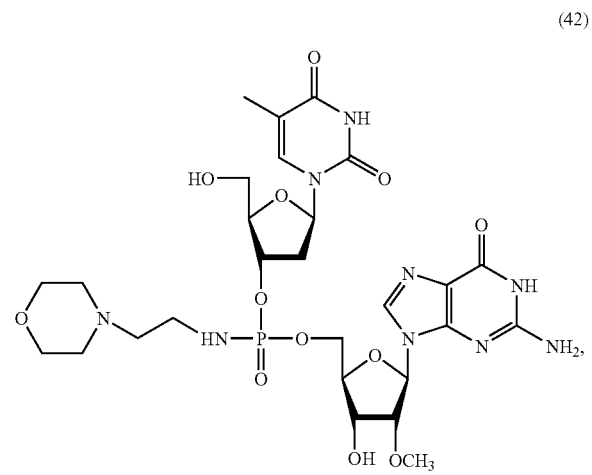
(43)
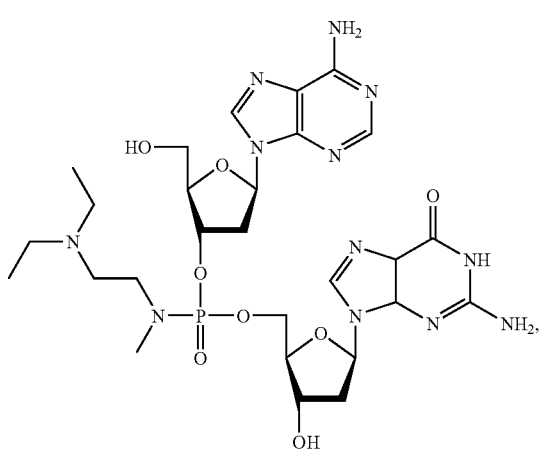
(44)
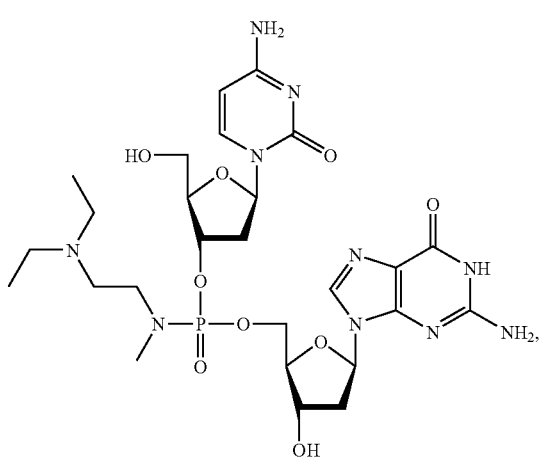

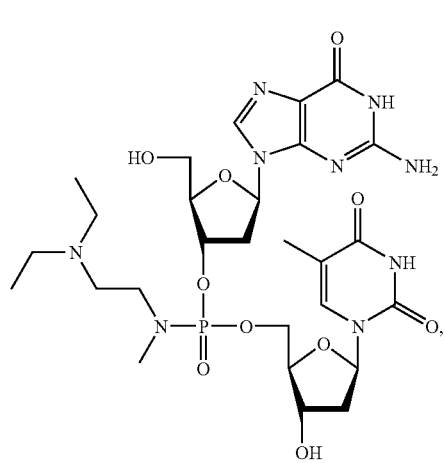
(45)
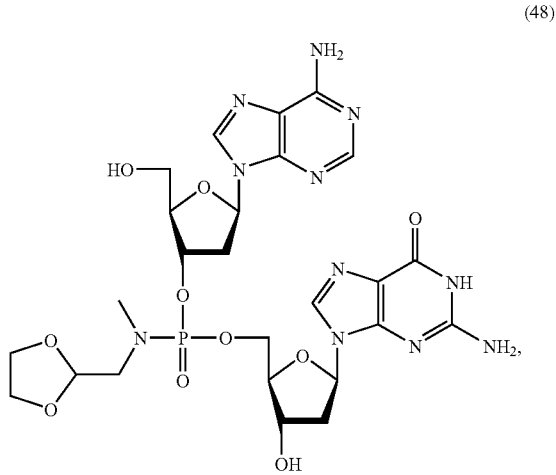
(48)
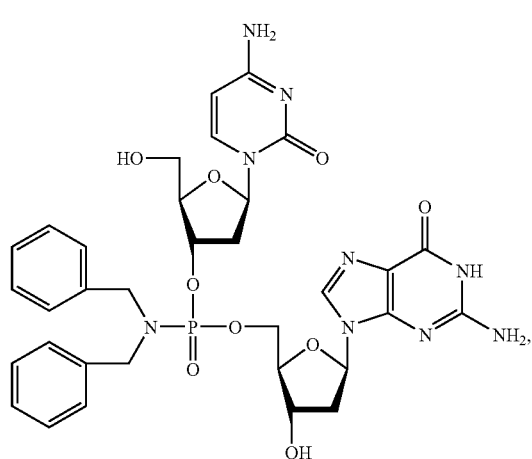
(46)
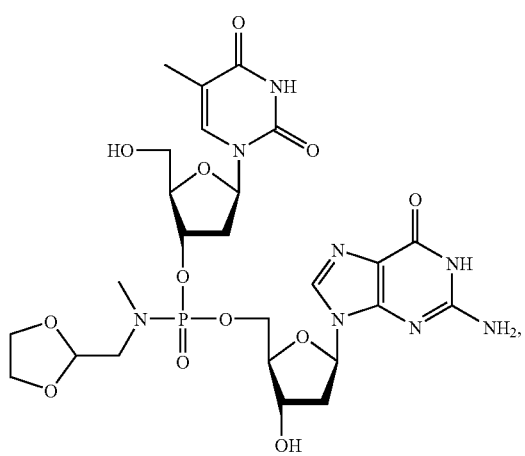
(49)
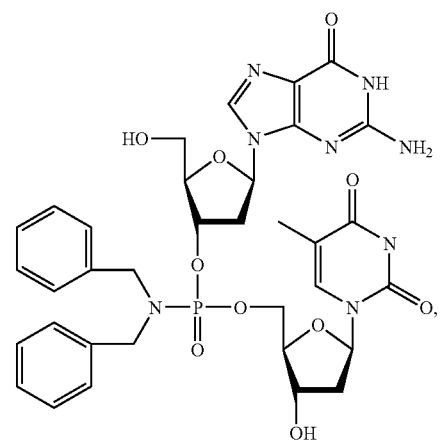
(47)
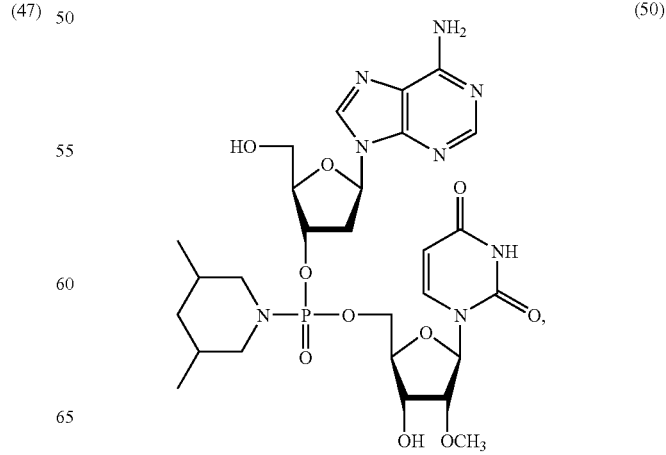
(50)

-continued
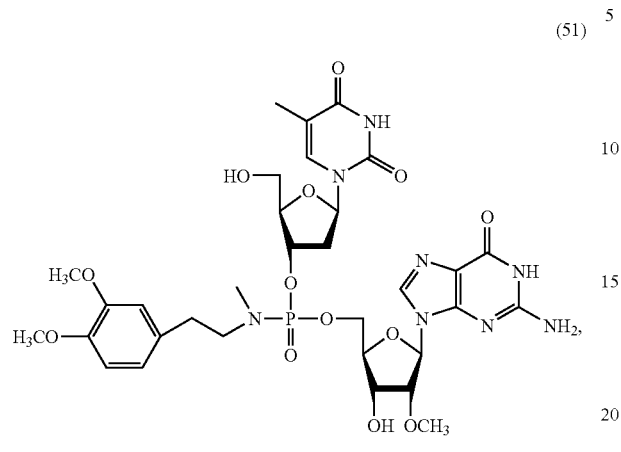
(51)
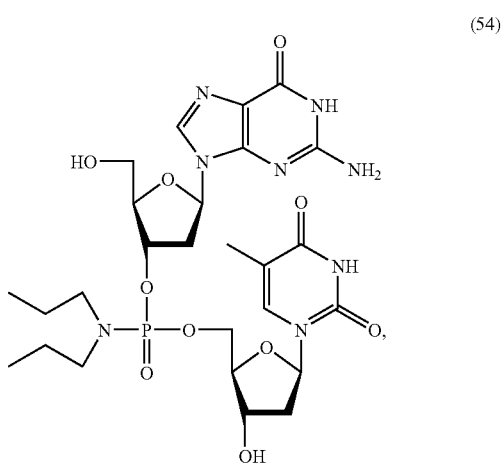
(54)
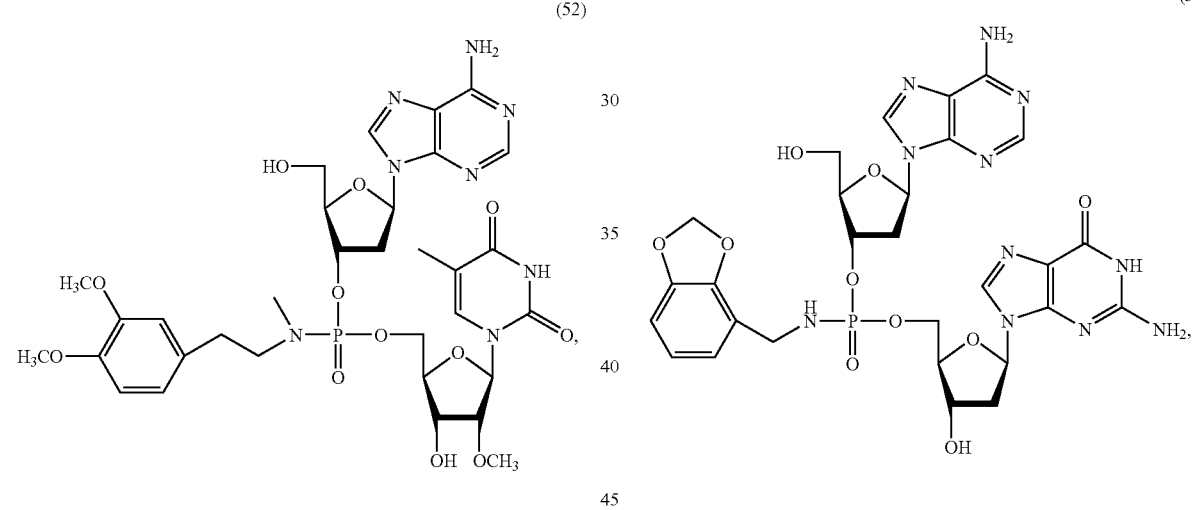
(52)
(55)
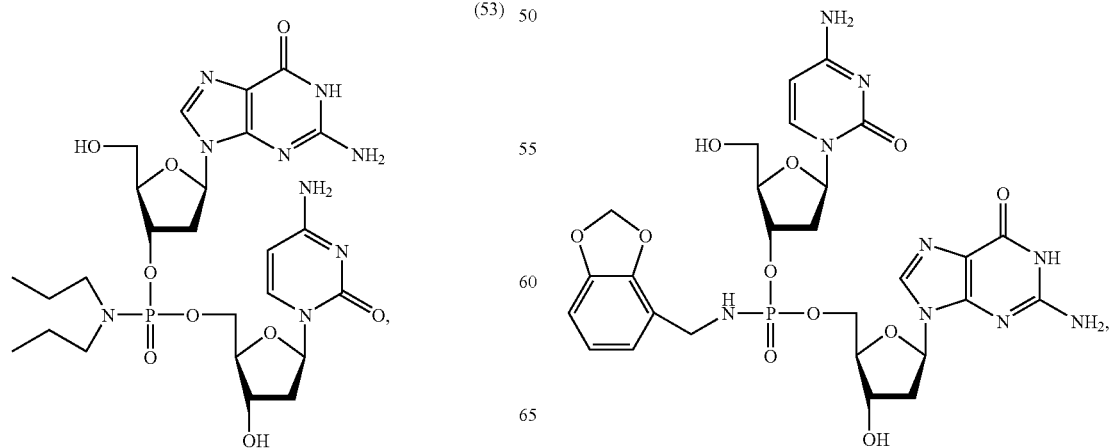
(53)
(56)

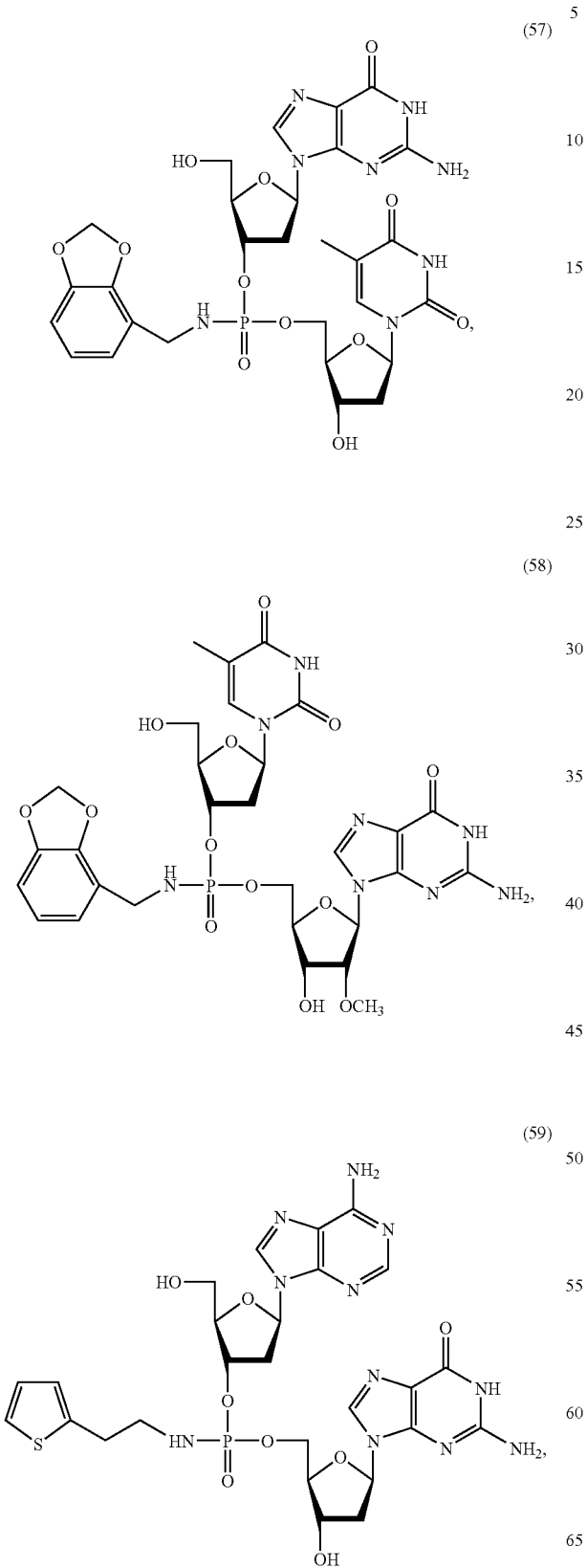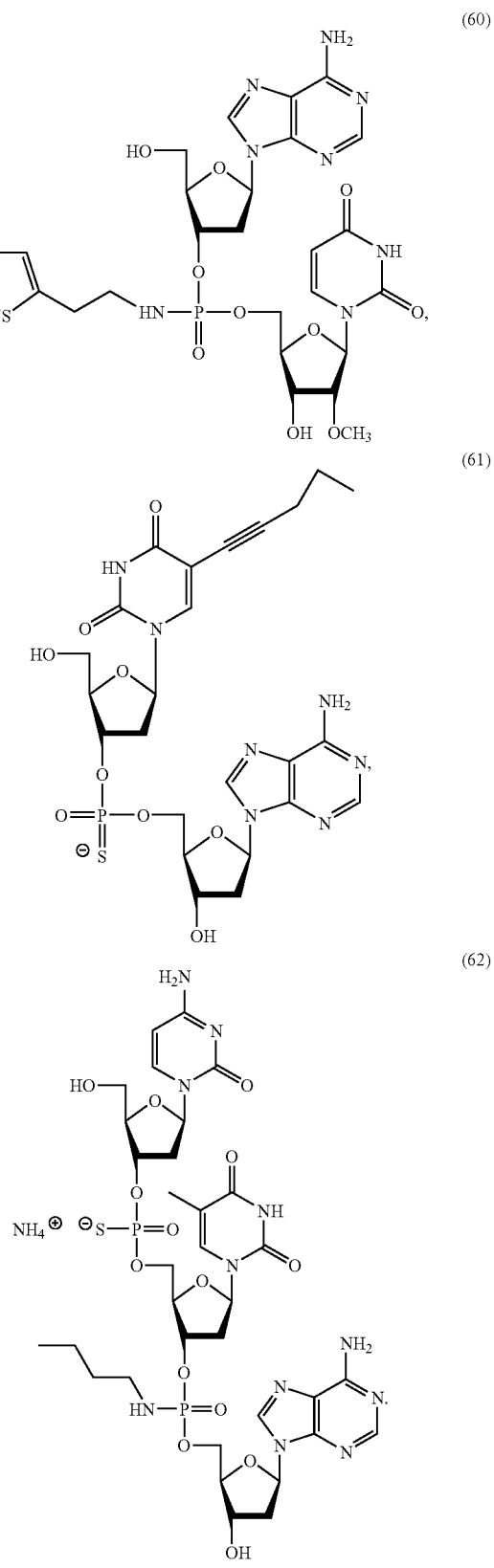

2. A pharmaceutical composition comprising the compound of claim 1 in combination with a pharmaceutically acceptable carrier.

3. The pharmaceutical composition of claim 2 wherein the pharmaceutically acceptable carrier comprises a lipid.

4. A pharmaceutical composition for treating a viral infection comprising a therapeutically effective amount of a compound of claim 1 in combination with a pharmaceutically acceptable carrier.

5. A pharmaceutical composition for treating an HBV infection comprising a therapeutically effective amount of a compound of claim 1 in combination with a pharmaceutically acceptable carrier.

6. A pharmaceutical composition for treating a viral infection comprising a therapeutically effective amount of a compound of claim 1 in combination with a therapeutically effective amount of a reverse transcriptase inhibitor and a pharmaceutically acceptable carrier.

7. A pharmaceutical composition of claim 6 wherein the reverse transcriptase inhibitor is 3TC.

8. A pharmaceutical composition of claim 5 wherein the HBV infection is a drug resistant HBV infection.

9. A compound selected from the group consisting of compounds 1-11, 13, 14, 16-18, 20-23, 25-28, 31-36, 38-42, 44, 46, 49-53, 56, 58, and 60-62, or a pharmaceutically acceptable salt thereof, wherein the compound is modified by the replacement of the internucleotide linkage with a different linkage selected from the group consisting of alkylphosphonate, phosphorothioate, phosphorodithioate, alkylphosphonothioate, phosphoroamidate, carbamate, carbonate, phosphate trimester, acetamidate, carboxymethyl ester linkages, and combinations thereof wherein the structures of compounds 3, 5, and 6 are as follows and wherein the structures of compounds 1, 2, 4, 7-11, 13, 14, 16-18, 20-23, 25-28, 31-36, 38-42, 44, 46, 49-53, 56, 58, and 60-62 are as set forth in claim 1:

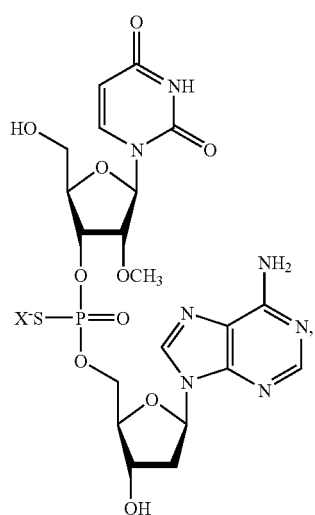

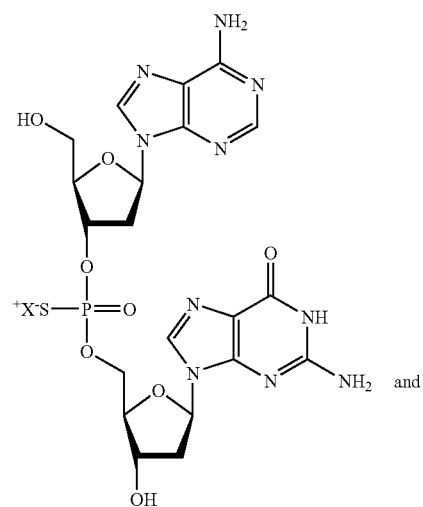

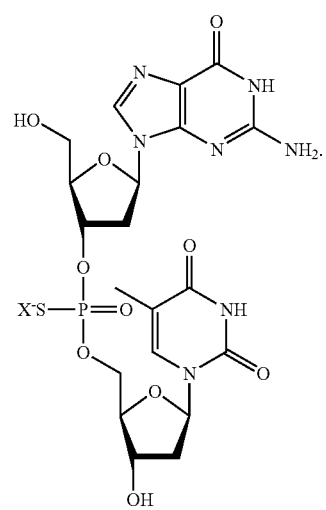

10. A compound selected from the group consisting of compounds 1-11, 13, 14 and 16-62 as set forth in claim 1 or claim 9 or a pharmaceutically acceptable salt thereof, wherein the compound is modified by replacement of the moiety at the 2' position of the sugar group with a different moiety selected from the group consisting of H, —OH, an amino group, a halogen group, a substituted or unsubstituted —O-lower alkyl group containing 1 to 6 saturated or unsaturated carbon atoms, a substituted or unsubstituted —O-aryl group having 2 to 6 carbons and a substituted or unsubstituted —O-allyl group having 2 to 6 carbon atoms.

11. A pharmaceutical composition comprising at least one compound selected from compounds 1, 2, and 4-11, 13, 14, 16-62 as set forth in claim 1 or claim 9 as specified above.

12. A pharmaceutical composition comprising a compound of claim 9 and a pharmaceutically acceptable carrier.

13. A pharmaceutical composition comprising a compound of claim 10 and a pharmaceutically acceptable carrier.

14. A method for treating a viral infection comprising administering to a patient an effective amount of a pharmaceutical composition of claim 11.

15. A method for treating an HBV infection comprising administering to a patient an effective amount of a pharmaceutical composition of claim 11.

16. A method for treating a viral infection comprising administering to a patient an effective amount of a pharmaceutical composition of claim 12.

17. A method for treating an HBV infection comprising administering to a patient an effective amount of a pharmaceutical composition of claim 12.

18. A method for treating a viral infection comprising administering to a patient an effective amount of a pharmaceutical composition of claim 13.

19. A method for treating an HBV infection comprising administering to a patient an effective amount of a pharmaceutical composition of claim 13.

20. A compound of claim 1 selected from compounds 18, 20, 31, 39, 50, 52, 60, or 61 having the structures as set forth in claim 1.

21. A pharmaceutical composition comprising at least one compound selected from compounds 19, 30, 45, 47, 54, or 57 having the structures as set forth in claim 1, or a pharmaceutically acceptable salt thereof, wherein the compound is modified by the replacement of the internucleotide linkage with a different linkage selected from the group consisting of alkylphosphonate, phosphorothioate, phosphorodithioate, alkylphosphonothioate, phosphoroamidate, carbamate, carbonate, phosphate trimester, acetamidate, carboxymethyl ester linkages, and combinations thereof.

22. A method for treating a viral infection comprising administering to a patient an effective amount of a pharmaceutical composition of claim 21.

23. A method for treating an HBV infection comprising administering to a patient an effective amount of a pharmaceutical composition of claim 21.

24. A compound selected from the group consisting of compounds 24, 29, 37, 43, 48, 55, and 59 having the structures as previously set forth in claim 1, or a pharmaceutically acceptable salt thereof, wherein the compound is modified by the replacement of the internucleotide linkage with a different linkage selected from the group consisting of alkylphosphonate, phosphorodithioate, alkylphosphonothioate, phosphoroamidate, carbamate, carbonate, phosphate trimester, acetamidate, carboxymethyl ester linkages, and combinations thereof.

* * * * *

UNITED STATES PATENT AND TRADEMARK OFFICE
CERTIFICATE OF CORRECTION

PATENT NO.        : 7,256,179 B2
APPLICATION NO.   : 11/057779
DATED             : August 14, 2007
INVENTOR(S)       : Radhakrishnan P. Iyer et al.

Page 1 of 3

It is certified that error appears in the above-identified patent and that said Letters Patent is hereby corrected as shown below:

Column 1

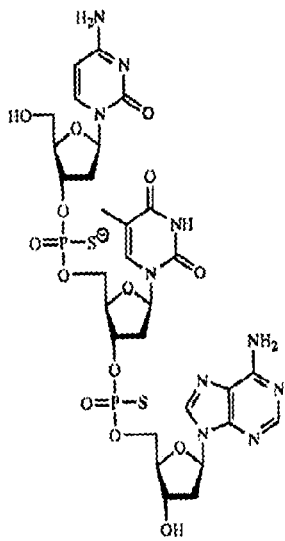

Compound (1), please delete " " and replace with

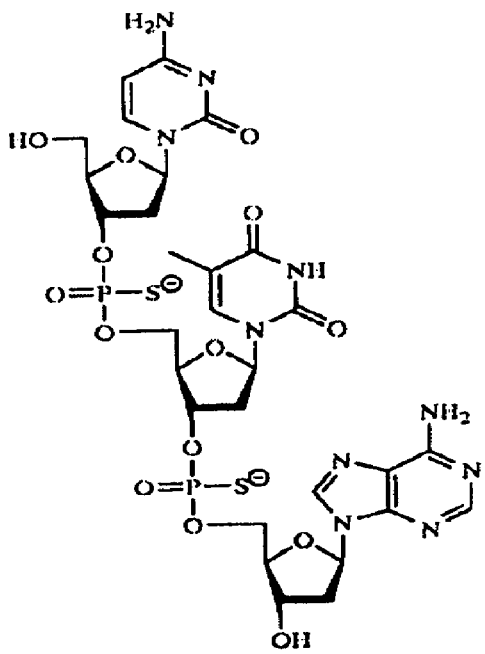

-- --

UNITED STATES PATENT AND TRADEMARK OFFICE
CERTIFICATE OF CORRECTION

PATENT NO. : 7,256,179 B2
APPLICATION NO. : 11/057779
DATED : August 14, 2007
INVENTOR(S) : Radhakrishnan P. Iyer et al.

It is certified that error appears in the above-identified patent and that said Letters Patent is hereby corrected as shown below:

Column 30

Claim 1, Compound (14), please delete " 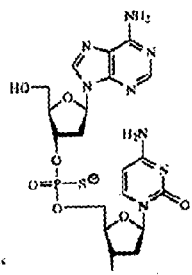 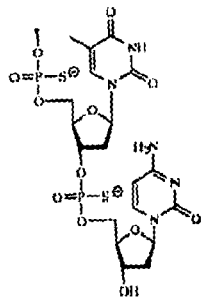 and replace with -- 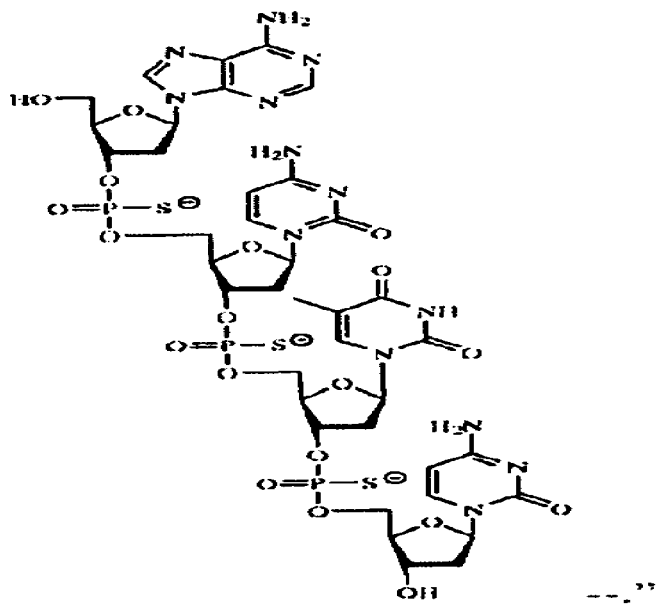 --."

UNITED STATES PATENT AND TRADEMARK OFFICE
CERTIFICATE OF CORRECTION

PATENT NO. : 7,256,179 B2 Page 3 of 3
APPLICATION NO. : 11/057779
DATED : August 14, 2007
INVENTOR(S) : Radhakrishnan P. Iyer et al.

It is certified that error appears in the above-identified patent and that said Letters Patent is hereby corrected as shown below:

Column 31

Claim 1, Compound 17, please delete " 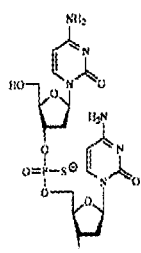 " and replace with -- 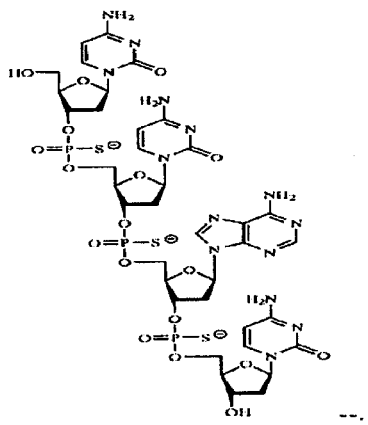 --.

Column 33

Claim 1, compound 22, line 28, please insert --(22)-- to the right of the compound."

Signed and Sealed this

Fifteenth Day of January, 2008

JON W. DUDAS
*Director of the United States Patent and Trademark Office*